United States Patent
Jarring et al.

(10) Patent No.: US 11,820,772 B2
(45) Date of Patent: Nov. 21, 2023

(54) POLYMORPHS OF THE HYDROCHLORIDE SALT OF LINAPRAZAN GLURATE

(71) Applicant: Cinclus Pharma Holding AB (Publ), Stockholm (SE)

(72) Inventors: Kjell Jarring, Lund (SE); Thomas Larsson, Bjarred (SE); Xingbang Lin, Guangdong (CN); Dan Wang, Guangdong (CN); Mikael Hillgren, Uppsala (SE)

(73) Assignee: Cinclus Pharma Holding AB (Publ), Stockholm (SE)

( * ) Notice: Subject to any disclaimer, the term of this patent is extended or adjusted under 35 U.S.C. 154(b) by 0 days.

(21) Appl. No.: 18/130,245

(22) Filed: Apr. 3, 2023

(65) Prior Publication Data

US 2023/0257378 A1    Aug. 17, 2023

Related U.S. Application Data

(63) Continuation of application No. PCT/EP2022/080850, filed on Nov. 4, 2022.

(30) Foreign Application Priority Data

Nov. 5, 2021   (WO) ............... PCT/CN2021/128918

(51) Int. Cl.
   *C07D 471/04* (2006.01)
(52) U.S. Cl.
   CPC ........ *C07D 471/04* (2013.01); *C07B 2200/13* (2013.01)
(58) Field of Classification Search
   CPC .................................................. C07D 471/04
   USPC ....................................................... 514/300
   See application file for complete search history.

(56) References Cited

U.S. PATENT DOCUMENTS

| | | |
|---|---|---|
| 2010/0063876 A1 | 3/2010 | Godden et al. |
| 2022/0002297 A1 | 1/2022 | Dahlstrom et al. |
| 2022/0362223 A1 | 11/2022 | Andersson et al. |

FOREIGN PATENT DOCUMENTS

| | | | |
|---|---|---|---|
| CN | 106279151 | * | 1/2017 |
| WO | WO 1999/055706 | | 11/1999 |
| WO | 02/085889 | * | 10/2002 |
| WO | WO 2002/098352 | | 12/2002 |
| WO | WO 2003/013472 | | 2/2003 |
| WO | WO 2006/076338 | | 7/2006 |
| WO | 2010/063876 | * | 6/2010 |
| WO | WO 2010/063876 | | 6/2010 |
| WO | 2021089580 | * | 5/2021 |
| WO | WO 2021/089580 | | 5/2021 |

OTHER PUBLICATIONS

Andersson et al., "The New P-CabX482 Was Safe, Tolerable and Provided 24H Intragastric Control, After Single Oral Doses in Healthy Volunteers," United European Gastroenterol. J. 2018, vol. 6(8S), p. A512-A513.
Design of Organic Solids, vol. 198, Jan. 1999, Chapter 5, pp. 163-208.
International Search Report and Written Opinion in International Appln. No. PCT/EP2020/080877, dated Feb. 5, 2021, 9 pages.
International Search Report and Written Opinion in International Appln. No. PCT/EP2022/080850, dated Jan. 5, 2023, 8 pages.
Office Action in Swedish Appln. No. 1951255-7, dated Mar. 27, 2020, 5 pages.
Search Report in Sweden Appln. No. 1951255-7, dated Mar. 27, 2020, 3 pages.
Unge et al., "A First-In-Human, Open-Label, Healthy Volunteer Study of the New P-Cab X842 Demonstrating 24H Acid Control for Treatment of Acid Related Diseases," Gastroenterology 2018, vol. 154, p. S-238.

* cited by examiner

*Primary Examiner* — Niloofar Rahmani
(74) *Attorney, Agent, or Firm* — Fish & Richardson P.C.

(57) ABSTRACT

The present invention relates to polymorphs of the hydrochloride salt of 5-{2-[({8-[(2,6-dimethylbenzyl)amino]-2,3-dimethylimidazo[1,2-a]pyridine-6-yl}carbonyl)-amino]ethoxy}-5-oxopentanoic acid (linaprazan glurate), more specifically Form 1 and Form 2 of the HCl salt of linaprazan glurate. The invention also relates to a process for the preparation of such polymorphs, to pharmaceutical compositions comprising such polymorphs, and to the use of these polymorphs in the treatment or prevention of gastrointestinal inflammatory diseases or gastric acid related diseases, in particular erosive gastroesophageal reflux disease (eGERD).

14 Claims, 16 Drawing Sheets

POLYMORPHS OF THE HYDROCHLORIDE SALT OF LINAPRAZAN GLURATE

CROSS-REFERENCE TO RELATED APPLICATIONS

Pursuant to 35 U.S.C. § 119(e), this application is a continuation of International Application No. PCT/EP2022/080850, filed on Nov. 4, 2022, which claims priority to International Application No. PCT/CN2021/128918, filed Nov. 5, 2021, the disclosures of the which are hereby incorporated by reference in their entirety.

TECHNICAL FIELD

The present invention relates to polymorphs of the hydrochloride salt of 5-{2-[({8-[(2,6-dimethylbenzyl)amino]-2,3-dimethylimidazo[1,2-a]pyridine-6-yl}carbonyl)-amino]ethoxy}-5-oxopentanoic acid (linaprazan glurate), more specifically Form 1 and Form 2 of the HCl salt of linaprazan glurate. The invention also relates to a process for the preparation of such polymorphs, to pharmaceutical compositions comprising such polymorphs, and to the use of these polymorphs in the treatment or prevention of gastrointestinal inflammatory diseases or gastric acid related diseases, in particular erosive gastroesophageal reflux disease (eGERD).

BACKGROUND

The compound linaprazan glurate (5-{2-[({8-[(2,6-dimethylbenzyl)amino]-2,3-dimethylimidazo[1,2-a]pyridine-6-yl}carbonyl)-amino]ethoxy}-5-oxopentanoic acid; previously known as X842) is disclosed in WO 2010/063876. Its structure is shown below. It is a potassium-competitive acid blocker (P-CAB), which competitively inhibits the gastric hydrogen potassium pump ($H^+/K^+$ ATPase) in the parietal cells. Linaprazan glurate may therefore be used to control the secretion of gastric acid in the stomach.

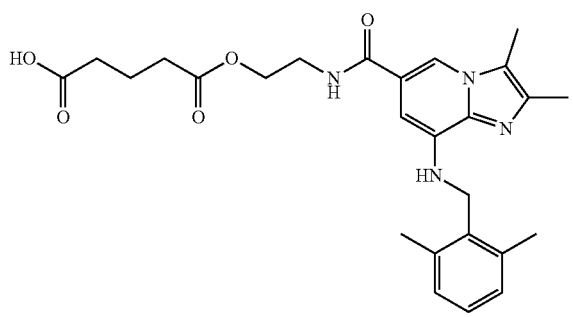 [SMILES: Cc1cccc(C)c1CNc1cc(C(=O)NCCOC(=O)CCCC(=O)O)cn2c(C)c(C)nc12]

Linaprazan glurate is a prodrug of linaprazan, which was disclosed in WO 99/55706 and previously studied in Phase I and II studies. These studies showed that linaprazan was well tolerated, with a fast onset of action and full effect at first dose. However, linaprazan was quickly eliminated from the body and had too short duration of acid inhibition. In comparison, linaprazan glurate has a longer half-life in the body and shows total control of the gastric acid production for a longer time compared to linaprazan. A clinical Phase I study has shown that administration of a single dose of linaprazan glurate can maintain the intragastric acidity above pH 4 for 24 hours. linaprazan glurate is therefore tailored for patients with severe erosive gastroesophageal reflux disease (eGERD).

For use in pharmaceutical preparations, it is desirable that the active pharmaceutical ingredient (API) is in a highly crystalline form. Non-crystalline (i.e., amorphous) materials may contain higher levels of residual solvents, which is undesirable. Also, because of their lower chemical and physical stability, as compared with crystalline material, amorphous materials may display faster decomposition and may spontaneously form crystals with a variable degree of crystallinity. This may result in unreproducible solubility rates and difficulties in storing and handling the material.

Two crystalline forms of the free base of linaprazan glurate are disclosed in CN 106279151. Forms A and B of the free base were found to be anhydrates, and Form A was shown to have a very low hygroscopicity. While Form A has good physical and chemical stability and can be obtained with high crystallinity, it is practically insoluble in water at pH 6.8, and only slightly soluble at pH 1. The low solubility restricts the development of formulations having desirable properties.

There is therefore a need for further crystalline forms of linaprazan glurate that have better properties than amorphous linaprazan glurate and the previously disclosed crystalline forms thereof. In particular, it is an object of the present invention to provide a stable crystalline form of linaprazan glurate that has good solubility, contains low levels of residual solvents, has a high chemical stability and low hygroscopicity and can be obtained in high levels of crystallinity.

DETAILED DESCRIPTION OF THE INVENTION

It has been discovered that the hydrochloride salt of linaprazan glurate under certain conditions may form stable crystalline forms (polymorphs). In addition to a high crystallinity and high chemical stability, these polymorphs have a significantly higher solubility than Forms A and B of the free base of linaprazan glurate. The new polymorphs are therefore expected useful in pharmaceutical compositions of linaprazan glurate. In a first aspect, therefore, the invention relates to a crystalline HCl salt of linaprazan glurate.

In some embodiments, the invention provides a crystalline HCl salt of linaprazan glurate wherein the crystalline HCl salt is stable at a relative humidity (RH) of 94% at room temperature. Such crystalline HCl salts can be stable under these conditions for at least 1 day, 1 week, 1 month, 3 months, 6 months, 1 year, 2 years, 3 years or even longer.

Figure 1:
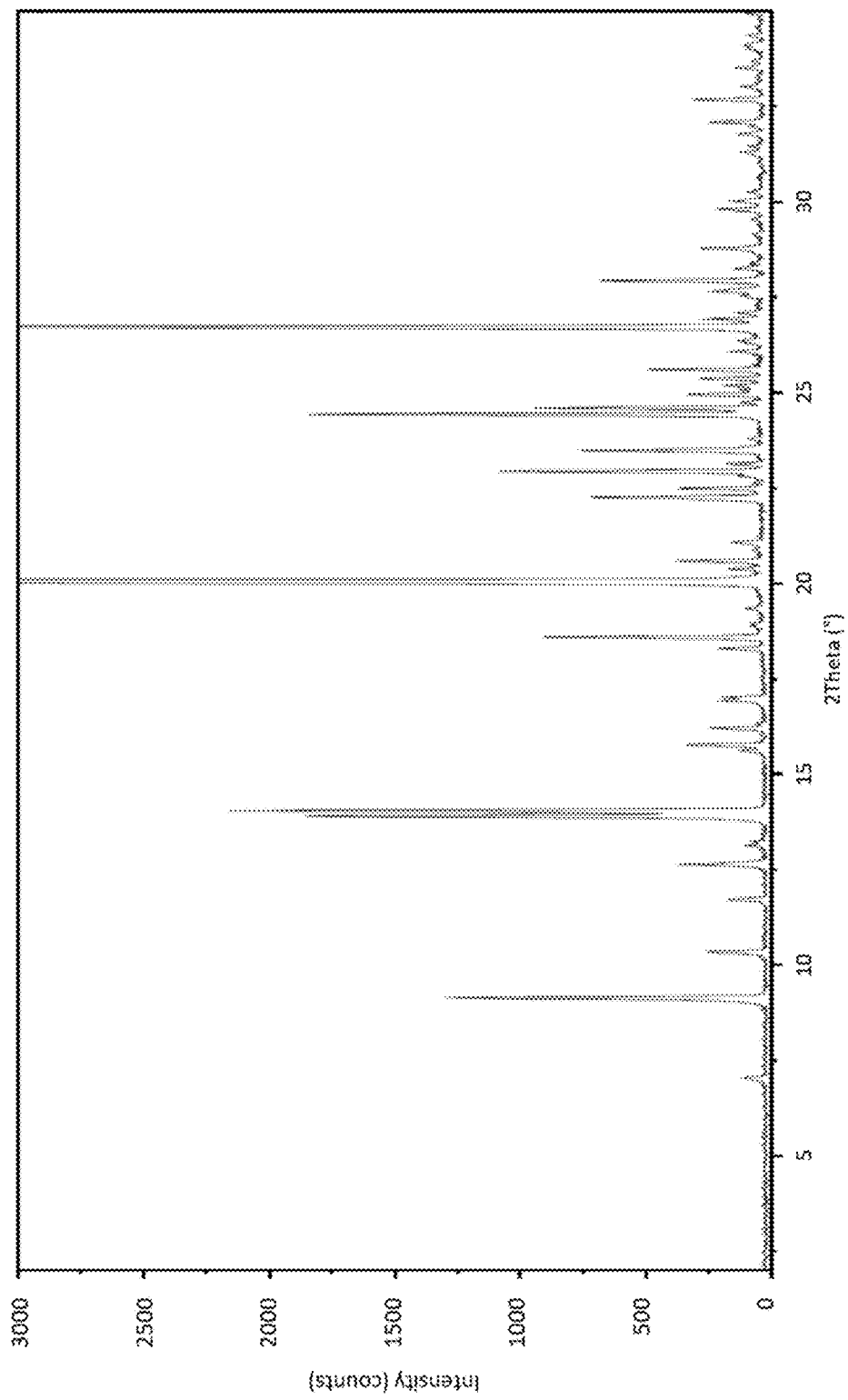
FIG. 1 shows the X-ray powder diffractogram of Form 1 of the HCl salt of linaprazan glurate, as obtained from a slurry in DMF.

In some embodiments, the crystalline HCl salt is an anhydrate. In a particular embodiment, the crystalline anhydrate is Form 1. This form may be prepared directly from the free base of linaprazan glurate, or by certain crystallisation techniques using the hydrochloride salt thereof, e.g. from a slurry in DMF, pyridine, benzyl alcohol or ethanol; by anti-solvent crystallisation from DMF or pyridine and certain anti-solvents; or by cooling from DMF or pyridine. In one embodiment, Form 1 has an X-ray powder diffraction (XRPD) pattern, obtained with CuKα1-radiation, with at least two peaks at °2θ values selected from the list consisting of 3.8±0.2, 9.1±0.2, 13.8±0.2, 14.0±0.2, 20.0±0.2, 22.9±0.2, 23.4±0.2, 24.4±0.2, 24.6±0.2 and 26.7±0.2. In some embodiments, Form 1 has an XRPD pattern, obtained with CuKα1-radiation, with at least peaks at °2θ values of 20.0±0.2 and 26.7±0.2. In some embodiments, Form 1 has an XRPD pattern, obtained with CuKα1-radiation, with at least four peaks at °2θ values selected from the list consisting of 3.8±0.2, 9.1±0.2, 13.8±0.2, 14.0±0.2, 20.0±0.2, 22.9±0.2, 23.4±0.2, 24.4±0.2, 24.6±0.2 and 26.7±0.2. In some embodiments, Form 1 has an XRPD pattern, obtained with CuKα1-radiation, with at least peaks at °2θ values of 20.0±0.2, 24.4±0.2, 24.6±0.2 and 26.7±0.2. In some embodiments, Form 1 has an XRPD pattern, obtained with CuKα1-radiation, with at least peaks at °2θ values of 20.0±0.2, 24.4±0.2, 24.6±0.2 and 26.7±0.2, and or more of 3.8±0.2, 9.1±0.2, 13.8±0.2, 14.0±0.2, 22.9±0.2 and 23.4±0.2. In some embodiments, Form 1 has an XRPD pattern, obtained with CuKα1-radiation, with at least peaks at °2θ values of 9.1±0.2, 13.8±0.2, 20.0±0.2, 23.4±0.2, 24.4±0.2, 24.6±0.2 and 26.7±0.2. In some embodiments, Form 1 has an XRPD pattern, obtained with CuKα1-radiation, with at least peaks at °2θ values of 3.8±0.2, 9.1±0.2, 13.8±0.2, 14.0±0.2, 20.0±0.2, 22.9±0.2, 23.4±0.2, 24.4±0.2, 24.6±0.2 and 26.7±0.2. In some embodiments, Form 1 has an XRPD pattern, obtained with CuKα1-radiation, with at least peaks at °2θ values of 3.8±0.2, 9.1±0.2, 13.8±0.2, 14.0±0.2, 20.0±0.2, 22.9±0.2, 23.4±0.2, 24.4±0.2, 24.6±0.2 and 26.7±0.2, and one or more of 16.2±0.2, 18.6±0.2, 22.2±0.2, 25.6±0.2 and 27.9±0.2. In a particular embodiment, the invention relates to Form 1, having an XRPD pattern, obtained with CuKα1-radiation, substantially as shown in FIG. 1. In a further embodiment, the invention relates to Form 1, having an XRPD pattern, obtained with CuKα1-radiation, substantially as shown in table 5. In some embodiments, Form 1 has a DSC curve comprising an endotherm between about 230° C. and about 240° C. In a particular embodiment, Form 1 has a DSC curve comprising an endotherm at approximately 233° C.

Dynamic vapour sorption analysis has shown that Form 1 has a very low hygroscopicity, with a water uptake of only about 0.2% at 90% RH. This low hygroscopicity is considered advantageous, as the water content of the crystals remains substantially constant even with humidity changes within the normal relative humidity range of about 30% to about 80% RH. In some embodiments, Form 1 is stable at a relative humidity up to 90% at a temperature of 25° C.

Figure 2:
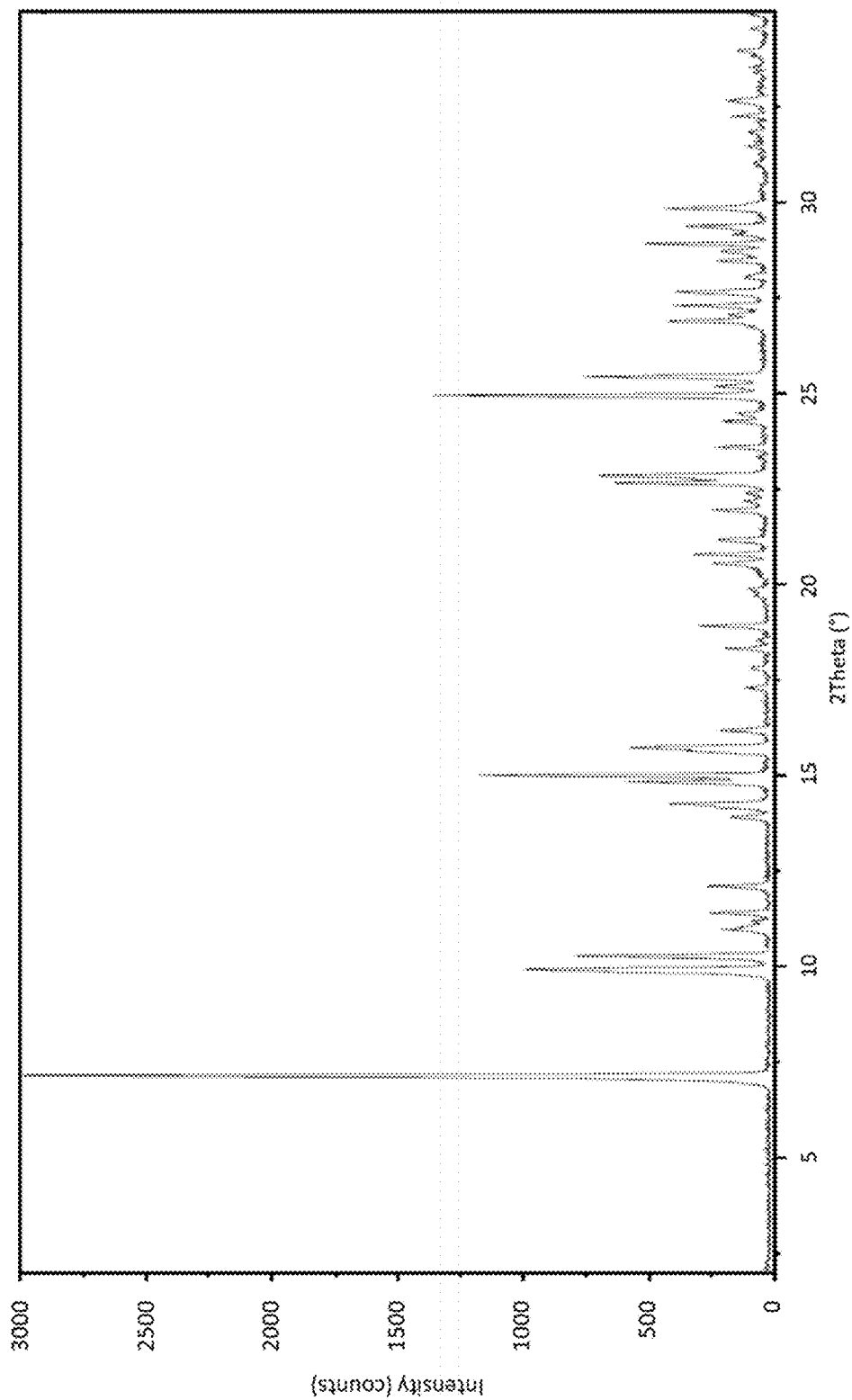
FIG. 2 shows the X-ray powder diffractogram of Form 2 of the HCl salt of linaprazan glurate, as obtained by cooling from a mixture of methanol and water ("sample 1").
Figure 3:
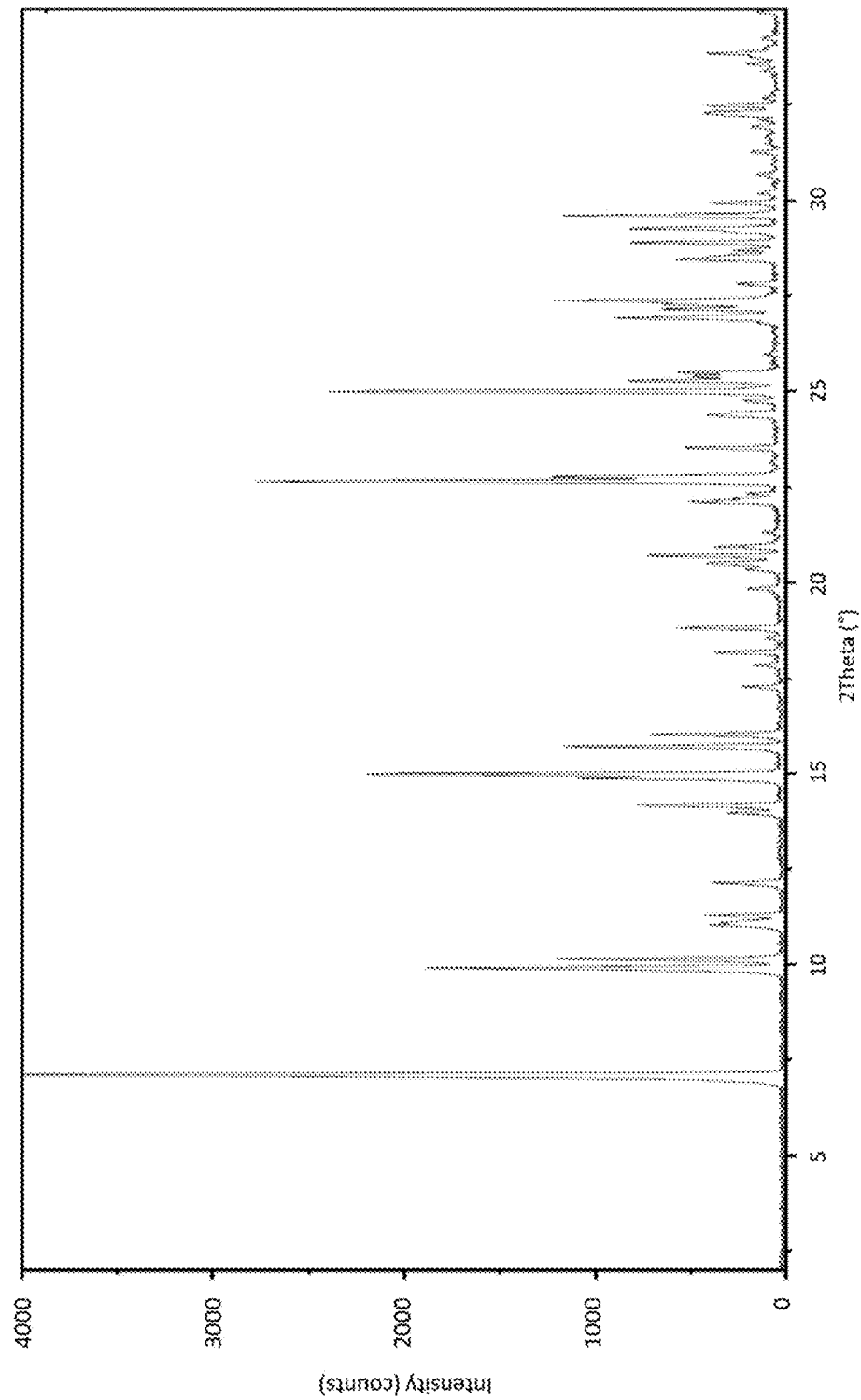
FIG. 3 shows the X-ray powder diffractogram of Form 2 of the HCl salt of linaprazan glurate, as obtained by cooling from methanol ("sample 2").

In some embodiments, the crystalline HCl salt is a hydrate, such as a non-stoichiometric hydrate. In a particular embodiment, the crystalline hydrate is Form 2. This form may be prepared directly from the free base of linaprazan glurate, or by certain crystallisation techniques using the hydrochloride salt thereof, e.g. from a slurry in acetic acid, methanol or a mixture of methanol and water; by evaporation from methanol; by anti-solvent crystallisation from methanol and certain anti-solvents; or by cooling from methanol or a mixture of methanol and water. In one embodiment, Form 2 has an X-ray powder diffraction (XRPD) pattern, obtained with CuKα1-radiation, with at least two peaks at °2θ values selected from the list consisting of 7.1±0.2, 9.9±0.2, 10.2±0.2, 15.0±0.2, 15.7±0.2, 22.6±0.2, 22.8±0.2 and 25.0±0.2. In some embodiments, Form 2 has an XRPD pattern, obtained with CuKα1-radiation, with at least peaks at °2θ values of 7.1±0.2 and 15.0±0.2, or at °2θ values of 7.1±0.2 and 25.0±0.2. In some embodiments, Form 2 has an XRPD pattern, obtained with CuKα1-radiation, with at least four peaks at °2θ values selected from the list consisting of 7.1±0.2, 9.9±0.2, 10.2±0.2, 15.0±0.2, 15.7±0.2, 22.6±0.2, 22.8±0.2 and 25.0±0.2. In some embodiments, Form 2 has an XRPD pattern, obtained with CuKα1-radiation, with at least peaks at °2θ values of 7.1±0.2, 15.0±0.2, 22.6±0.2 and 25.0±0.2. In some embodiments, Form 2 has an XRPD pattern, obtained with CuKα1-radiation, with at least six peaks at °2θ values selected from the list consisting of 7.1±0.2, 9.9±0.2, 10.2±0.2, 15.0±0.2, 15.7±0.2, 22.6±0.2, 22.8±0.2 and 25.0±0.2. In some embodiments, Form 2 has an XRPD pattern, obtained with CuKα1-radiation, with at least peaks at °2θ values of 7.1±0.2, 9.9±0.2, 10.2±0.2, 15.0±0.2, 15.7±0.2, 22.6±0.2, 22.8±0.2 and 25.0±0.2. In a particular embodiment, the invention relates to Form 2, having an XRPD pattern, obtained with CuKα1-radiation, substantially as shown in FIG. 2 or FIG. 3. In a further embodiment, the invention relates to Form 2, having an XRPD pattern, obtained with CuKα1-radiation, substantially as shown in table 6 or 7.

In some embodiments, Form 2 has a DSC curve comprising an endotherm between about 175° C. and about 185° C. In a particular embodiment, Form 2 has a DSC curve comprising an endotherm at approximately 180° C.

It has been found that the water content of Form 2 can vary between about 0 and 5%, depending on the relative humidity. Between about 20 and 90% RH, the water uptake of Form 2 increases almost linearly with increasing relative humidity. The crystalline non-stoichiometric hydrate may therefore be characterized as a channel hydrate. In some embodiments, Form 2 is stable at a relative humidity up to 90% at a temperature of 25° C.

Figure 12:
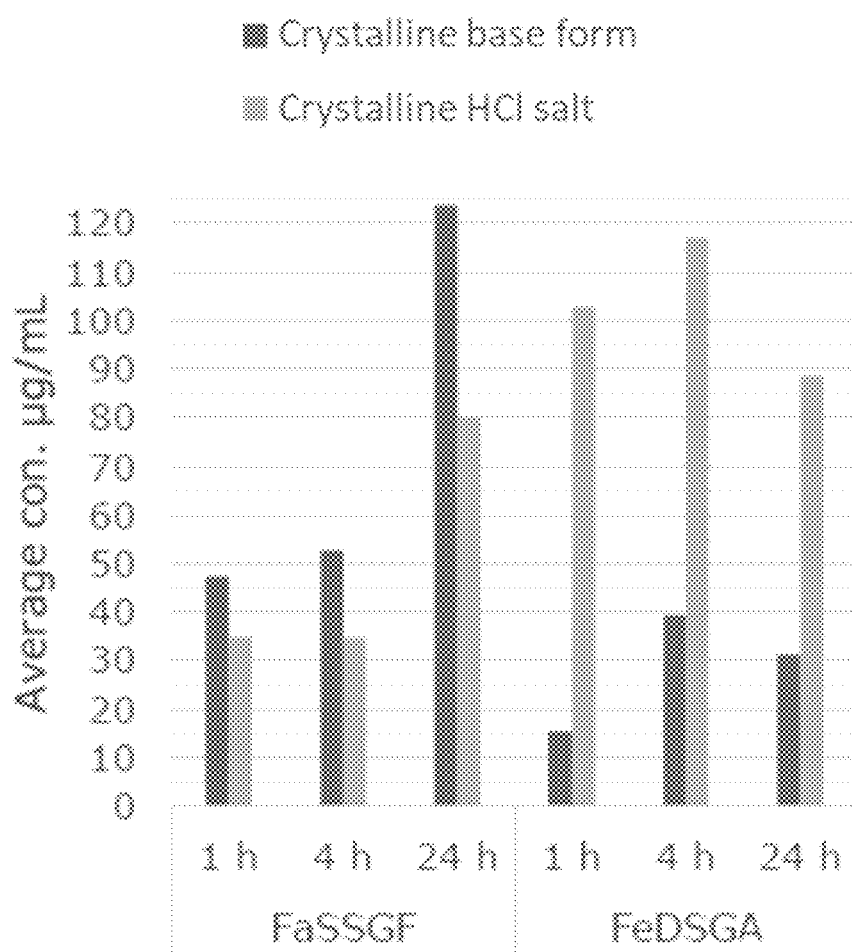
FIG. 12 shows a comparison of the solubility (μg/mL) of the free base and the HCl salt of linaprazan glurate in media simulating gastric fluid (FaSSGF and FeDSGA).

As described in the experimental section, solubility experiments have shown that the crystalline free base and the crystalline HCl salt behave somewhat differently at low and medium low pH (see FIG. 12). In medium simulating fasted state gastric fluid (FaSSGF; pH 1.6), the solubility of the free base was about 1.4 times higher than that of the HCl salt after 1 hour of incubation. Surprisingly, however, in medium simulating fed state gastric fluid (FeDSGA; pH 5.0), the relative solubility of the two crystalline materials was reversed, with the HCl salt being more than 6.5 times more soluble than the free base after 1 hour of incubation. The increased solubility of the crystalline HCl salt at higher pH is considered useful, not least as the pH of the stomach will be raised during ongoing treatment with linaprazan glurate.

Figure 13A:
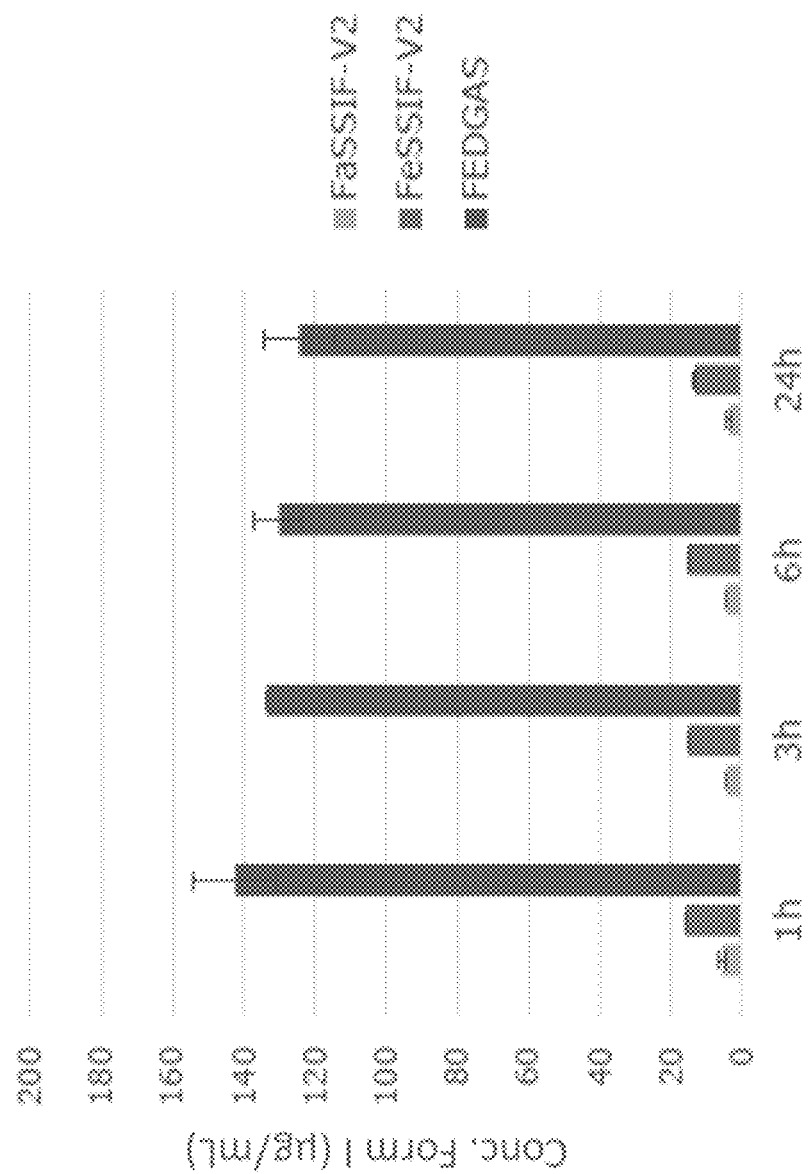
FIGS. 13A and 13B show the solubility (μg/mL) of Form 1 and Form 2, respectively, in media simulating gastric and intestinal fluids (FaSSIF-V2, FeSSIF-V2 and FEDGAS).
Figure 13B:
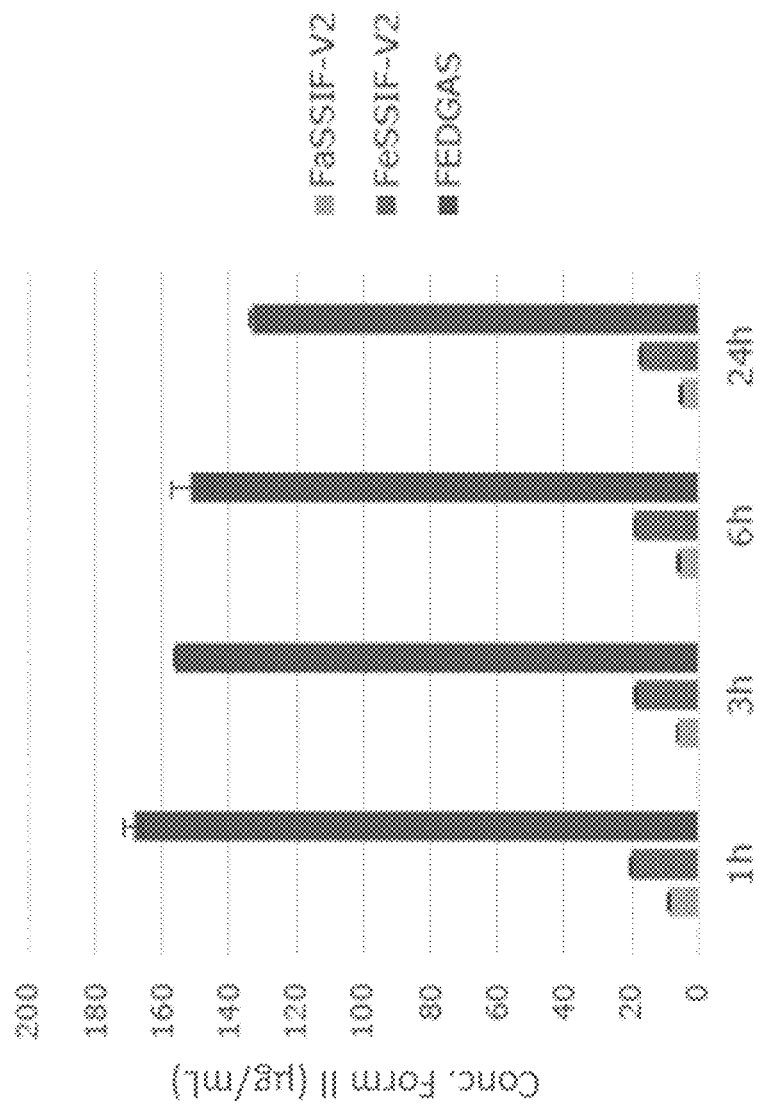

It has also been found that the two crystalline HCl salts have higher solubility in gastric fluid (fed state) than in intestinal fluid (fed or fasted state); see FIGS. 13A and 13B.

In another aspect, the invention relates to a process for the preparation of Form 1 of the HCl salt of linaprazan glurate. Form 1 may be prepared directly from the free base of linaprazan glurate, or by certain crystallisation techniques using amorphous or partially crystalline hydrochloride salt of linaprazan glurate, as is described in the appended examples. Alternatively, Form 1 may be prepared via Form 2 as an intermediate. It has been discovered that this route is more suitable for large scale preparation of Form 1, and allows the product to be prepared with considerably lower residual solvent levels than when Form 1 is prepared directly from the free base of linaprazan glurate.

In some embodiments, therefore, the process for the preparation of Form 1 of the HCl salt of linaprazan glurate comprises the steps of:
  a) preparing a suspension of Form 2 of the HCl salt in a suitable solvent, such as ethyl acetate;
  b) slurrying the suspension of step a) until conversion of Form 1 to Form 2 of the HCl salt is completed;
  c) recovering the solid obtained in step b); and
  d) drying the solid of step c), such as under vacuum and/or at elevated temperature.

Step b) is preferably performed at a temperature between about 25 and about 40° C., and more preferably at about 30° C. The suspension is preferably slurried for at least 6 hours, more preferably for at least 12 hours, more preferably for at least 18 hours and even more preferably for at least 24 hours. Drying step c) is preferably performed under vacuum and at elevated temperature such as at about 50° C., about 55° C., about 60° C., about 65° C. or about 70° C.

Crystalline Form 2 of the HCl salt may be prepared from the amorphous or partially crystalline hydrochloride salt, as described in the appended examples, or directly from the free base of linaprazan glurate. In a further embodiment, therefore, the process for the preparation of Form 1 of the HCl salt of linaprazan glurate comprises the steps of:
  a) preparing a solution of the free base of linaprazan glurate in acetic acid;
  b) adding ethyl acetate;
  c) adding concentrated hydrochloric acid, and maintaining stirring until Form 2 of the HCl salt is obtained;
  d) recovering the solid obtained in step c);
  e) adding ethyl acetate to the solid of step d);
  f) slurrying the suspension of step e) until conversion of Form 2 to Form 1 of the HCl salt is completed;
  g) recovering the solid obtained in step f); and
  h) drying the solid of step g), such as under vacuum and/or at elevated temperature.

One or more in-line filtration steps may optionally be performed following steps a) and/or b), in order to remove any insoluble material or microparticles from the solution of linaprazan glurate. Seed crystals may optionally be used to induce crystallisation in step f). Step f) is preferably performed at a temperature between about 25 and about 40° C., and more preferably at about 30° C. The suspension is preferably slurried for at least 6 hours, more preferably for at least 12 hours, more preferably for at least 18 hours and even more preferably for at least 24 hours. Drying step h) is preferably performed under vacuum and at elevated temperature such as at about 50° C., about 55° C., about 60° C., about 65° C. or about 70° C.

In another aspect, the invention relates to a pharmaceutical composition comprising a therapeutically effective amount of a crystalline HCl salt of linaprazan glurate as disclosed herein, in association with one or more pharmaceutically acceptable excipients. The excipients may e.g. include fillers, binders, surfactants, disintegrants, glidants and lubricants. In some embodiments, the crystalline HCl salt of linaprazan glurate is Form 1. In some embodiments, the crystalline HCl salt of linaprazan glurate is Form 2.

In some embodiments, the pharmaceutical composition comprises a crystalline HCl salt of linaprazan glurate, such as Form 1 or Form 2, having a polymorphic purity of at least about 90%. In some embodiments, the polymorphic purity is at least about 95%. In some embodiments, the polymorphic purity is at least about 98%. For example, the polymorphic purity may be at least about 98.5%, such as at least about 99%, such as at least about 99.5%, such as at least about 99.8%, or such as at least about 99.9%. In some embodiments, a pharmaceutical composition comprising a crystalline HCl salt of linaprazan glurate is substantially free of other forms of linaprazan glurate. For example, in some embodiments, a pharmaceutical composition comprising Form 1 is substantially free of other forms of linaprazan glurate, such as Form 2 of linaprazan glurate. In some embodiments, Form 1 contains less than about 15% by weight of Form 2 or any other polymorph of linaprazan glurate. For example, Form 1 contains less than about 14%, about 13%, about 12%, about 11%, about 10%, about 9%, about 8%, about 7%, about 6%, about 5%, about 4%, about 3%, about 2%, about 1% or less by weight of Form 2 or any other polymorph of linaprazan glurate. In other embodiments, Form 2 contains less than about 15% by weight of Form 1 or any other polymorph of linaprazan glurate. For example, Form 2 contains less than about 14%, about 13%, about 12%, about 11%, about 10%, about 9%, about 8%, about 7%, about 6%, about 5%, about 4%, about 3%, about 2%, about 1% or less by weight of Form 1 or any other polymorph of linaprazan glurate.

In some embodiments, the pharmaceutical composition can comprise between about 1% and about 100%, such as between about 1% and about 50%, or such as between about 1% and about 20% by weight of a crystalline HCl salt of linaprazan glurate. For example, the composition can comprise between about 1% and about 15%, or between about 5% and about 20%, such as between about 1% and about 10%, between about 5% and about 15%, and between about 10% and about 20%, or such as between about 1% and about 5%, between about 5% and about 10%, between about 10% and about 15%, and between about 15% and about 20% by weight of a crystalline HCl salt of linaprazan glurate. In some embodiments, the composition comprises about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2% or about 1% by weight of a crystalline HCl salt of linaprazan glurate.

In some embodiments, the composition comprises a unit dose of about 25 mg to about 150 mg of a crystalline HCl salt of linaprazan glurate. For example, the composition can comprise between about 25 mg and about 50 mg, between about 50 mg and about 75 mg, between about 75 mg and about 100 mg, between about 100 mg and about 125 mg, or between about 125 mg and about 150 mg. In some embodiments, the composition comprises about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, or about 150 mg of a crystalline HCl salt of linaprazan glurate. The daily dose can be administered as a single dose or divided into two, three or more unit doses.

In some embodiments, the pharmaceutical composition comprises a surfactant. The surfactant may be a cationic surfactant, an anionic surfactant or a nonionic surfactant. Examples of cationic surfactants include, but are not limited to, cetyltrimethylammonium bromide (cetrimonium bromide) and cetylpyridinium chloride. Examples of anionic surfactants include, but are not limited to, sodium dodecyl sulfate (sodium lauryl sulfate) and ammonium dodecyl sulfate (ammonium lauryl sulfate). Examples of nonionic surfactants include, but are not limited to, glycerol monooleate, glycerol monostearate, polyoxyl castor oil (Cremophor EL), poloxamers (e.g., poloxamer 407 or 188), polysorbate 80 and sorbitan esters (Tween).

In some embodiments, the pharmaceutical composition comprises a filler. Examples of suitable fillers include, but are not limited to, dicalcium phosphate dihydrate, calcium sulfate, lactose (such as lactose monohydrate), sucrose, mannitol, sorbitol, cellulose, microcrystalline cellulose, dry starch, hydrolyzed starches and pregelatinized starch.

In some embodiments, the pharmaceutical composition comprises a binder. Examples of suitable binders include, but are not limited to, starch, pregelatinized starch, gelatin, sugars (such as sucrose, glucose, dextrose, lactose and sorbitol), polyethylene glycol, waxes, natural and synthetic gums (such as acacia gum and tragacanth gum), sodium alginate, cellulose derivatives (such as hydroxypropylmethylcellulose (or hypromellose), hydroxypropylcellulose and ethylcellulose) and synthetic polymers (such as acrylic acid and methacrylic acid copolymers, methacrylic acid copolymers, methyl methacrylate copolymers, aminoalkyl methacrylate copolymers, polyacrylic acid/polymethacrylic acid copolymers and polyvinylpyrrolidone (povidone)).

In some embodiments, the pharmaceutical composition comprises a disintegrant. Examples of suitable disintegrants include, but are not limited to, dry starch, modified starch (such as (partially) pregelatinized starch, sodium starch glycolate and sodium carboxymethyl starch), alginic acid, cellulose derivatives (such as sodium carboxymethylcellulose, hydroxypropyl cellulose, and low substituted hydroxypropyl cellulose (L-HPC)) and cross-linked polymers (such as carmellose, croscarmellose sodium, carmellose calcium and cross-linked PVP (crospovidone)).

In some embodiments, the pharmaceutical composition comprises a glidant or lubricant. Examples of suitable glidants and lubricants include, but are not limited to, talc, magnesium stearate, calcium stearate, sodium stearyl fumarate, stearic acid, glyceryl behenate, colloidal anhydrous silica, aqueous silicon dioxide, synthetic magnesium silicate, fine granulated silicon oxide, starch, sodium lauryl sulfate, boric acid, magnesium oxide, waxes (such as carnauba wax), hydrogenated oil, polyethylene glycol, sodium benzoate, polyethylene glycol, and mineral oil.

In general, pharmaceutical compositions may be prepared in a conventional manner using conventional excipients. In some embodiments, the ingredients of the formulation are mixed to a homogenous mixture and then formulated as tablets or capsules. The homogenous mixture of the ingredients may be compressed into tablets using conventional techniques, such as a rotary tablet press. The mixture of ingredients may also be granulated. For instance, the mixture of ingredients may be wetted by the addition of a liquid, such as water and/or an appropriate organic solvent (e.g., ethanol or isopropanol), and thereafter granulated and dried. Alternatively, granules may be prepared by dry granulation, such as by roller compaction. The granules obtained may be compressed into tablets using conventional techniques. Capsules may comprise a powder mixture or small multiparticulates (such as granules, extruded pellets or minitablets) of the ingredients. If desirable, any of the tablets, capsules, granules, extruded pellets and minitablets mentioned above may be coated with one or more coating layers. Such coating layers may be applied by methods known in the art, such as by film coating involving perforated pans and fluidized beds. In some embodiments, the formulation is in the form of a tablet.

Following absorption into the blood stream, linaprazan glurate is quickly metabolized into linaprazan, which is the active metabolite. Whereas the plasma concentration of linaprazan glurate is only very low and difficult to determine, the plasma concentration of linaprazan may be determined instead. Phase I studies have indicated that certain doses of linaprazan glurate should be able to maintain the intra-gastric pH above 4 for 24 hours after administration. It is estimated that this requires a minimal plasma concentration ($C_{min}$) of linaprazan of at least about 240 nmol/L after 22 hours. At such doses, a once daily oral administration of the formulation would be sufficient. In some embodiments, therefore, a single unit dose of a pharmaceutical composition of linaprazan glurate provides a $C_{min}$ of linaprazan in a human of at least about 240 nmol/L after 22 hours following oral administration of the pharmaceutical composition to said human. In other embodiments, a daily administration of two unit doses of a pharmaceutical composition of linaprazan glurate provides a $C_{min}$ of linaprazan in a human of at least about 240 nmol/L after 10 hours following oral administration of the last unit dose of the pharmaceutical composition to said human.

In one aspect, the invention relates to the crystalline forms of the HCl salt of linaprazan glurate as disclosed herein, for use in therapy.

The crystalline forms of the HCl salt of linaprazan glurate disclosed herein can be used in the treatment or prevention of diseases or conditions wherein inhibition of gastric acid secretion is necessary or desirable, such as in *H. pylori* eradication. Examples of such diseases and conditions include gastrointestinal inflammatory diseases and gastric acid related diseases, such as gastritis, gastroesophageal reflux disease (GERD), erosive gastroesophageal reflux disease (eGERD), *H. pylori* infection, Zollinger-Ellison syndrome, peptic ulcer disease (including gastric ulcers and duodenal ulcers), bleeding gastric ulcer, symptoms of gastroesophageal reflux disease (including heartburn, regurgitation and nausea), gastrinoma and acute upper gastrointestinal bleeding.

In one aspect, therefore, the invention relates to a method for treating or preventing a gastrointestinal inflammatory disease or a gastric acid related disease in a subject in need thereof, comprising administering a pharmaceutical composition comprising a therapeutically effective amount of a crystalline form of the HCl salt of linaprazan glurate, as disclosed herein. In some embodiments, the crystalline form of the HCl salt of linaprazan glurate is Form 1. In some embodiments, the crystalline form of the HCl salt of linaprazan glurate is Form 2.

In some embodiments, the treatment of GERD is on-demand treatment of GERD.

In another aspect, the invention relates to a pharmaceutical composition comprising a therapeutically effective amount of a crystalline HCl salt of linaprazan glurate, as disclosed herein, for use in the treatment or prevention of a gastrointestinal inflammatory disease or a gastric acid related disease.

As used herein, the term "polymorph" refers to crystals of the same molecule that have different physical properties as a result of the order of the molecules in the crystal lattice. Polymorphs of a single compound have one or more different chemical, physical, mechanical, electrical, thermodynamic, and/or biological properties from each other. Differences in physical properties exhibited by polymorphs can affect pharmaceutical parameters such as storage stability, compressibility, density (important in composition and product manufacturing), dissolution rates (an important factor in determining bioavailability), solubility, melting point, chemical stability, physical stability, powder flowability, water sorption, compaction, and particle morphology. Differences in stability can result from changes in chemical reactivity (e.g. differential oxidation, such that a dosage form discolours more rapidly when comprised of one polymorph than when comprised of another polymorph) or mechanical changes (e.g., crystal changes on storage as a kinetically favoured polymorph converts to a thermodynamically more stable polymorph) or both (e.g., one polymorph is more hygroscopic than the other). As a result of solubility/dissolution differences, some transitions affect potency and/or toxicity. In addition, the physical properties of the crystal may be important in processing; for example, one polymorph might be more likely to form solvates or might be difficult to filter and wash free of impurities (i.e., particle shape and size distribution might be different between one polymorph relative to the other). "Polymorph" does not include amorphous forms of the compound.

As used herein, the term "amorphous" refers to a non-crystalline form of a compound which may be a solid state form of the compound or a solubilized form of the compound. For example, "amorphous" refers to a compound without a regularly repeating arrangement of molecules or external face planes.

As used herein, the term "anhydrate" or "anhydrous form" refers to a polymorph of linaprazan glurate that has 0.5% or less by weight water, for example 0.4% or less, or 0.3% or less, or 0.2% or less, or 0.1% or less by weight water.

As used herein, the term "polymorphic purity" when used in reference to a composition comprising a polymorph of linaprazan glurate, refers to the percentage of one specific polymorph relative to another polymorph or an amorphous form of linaprazan glurate in the referenced composition. For example, a composition comprising Form 1 having a polymorphic purity of 90% would comprise 90 weight parts of Form 1 and 10 weight parts of other crystalline and/or amorphous forms of linaprazan glurate.

As used herein, the terms "effective amount" or "therapeutically effective amount" refer to a sufficient amount of linaprazan glurate that, following administration to a subject, will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic use is the amount of linaprazan glurate required to provide a clinically significant decrease in disease symptoms. An appropriate "effective" amount in any individual case is determined using any suitable technique, such as a dose escalation study.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "pharmaceutically acceptable" refers to those compounds, materials, compositions and/or dosage forms that are suitable for human pharmaceutical use and that are generally safe, non-toxic and neither biologically nor otherwise undesirable.

As used herein, a compound or composition is "substantially free" of one or more other components if the compound or composition contains no significant amount of such other components. Such components can include impurities such as starting materials, residual solvents, or any other impurities that can result from the preparation of and/or isolation of the compounds and compositions provided herein. In some embodiments, a polymorph provided herein is "substantially free" from impurities. The purity of a particular polymorph is preferably greater than about 90% (w/w), such as greater than about 95% (w/w), such as greater than about 97% (w/w), or such as greater than about 99% (w/w). In some embodiments, the purity of a particular polymorph is greater than 99.5% (w/w), or even greater than 99.9% (w/w). In some embodiments, the impurity in a particular polymorph is less than about 1% (w/w), such as less than about 0.5% (w/w), or such as less than about 0.1% (w/w). The total amount of impurities may be determined e.g. by high-performance liquid chromatography (HPLC) methods.

In some embodiments, a polymorph form provided herein is substantially free of other polymorph forms. In some embodiments, a particular polymorph of linaprazan glurate is "substantially free" of other polymorphs if the particular polymorph constitutes at least about 95% by weight of linaprazan glurate present. In some embodiments, a particular polymorph of linaprazan glurate is "substantially free" of other polymorphs if the particular polymorph constitutes at least about 97%, about 98%, about 99%, or about 99.5% by weight of linaprazan glurate present.

As used herein, a compound is "substantially present" as a given polymorph if at least about 50% by weight of the compound is in the form of that polymorph, for example if at least about 60%, at least about 70%, at least about 80%, or at least about 90% by weight of the compound is in the form of that polymorph. In some embodiments, at least about 95%, such as at least about 96%, such as at least about 97%, such as at least about 98%, such as at least about 99% or such as at least about 99.5% by weight of the compound is in the form of that polymorph.

As used herein, the term "stable" means that the polymorphs do not exhibit a change in one or more of polymorph form (e.g., an increase or decrease of a certain form), appearance, pH, percent impurities, activity (as measured by in vitro assays), or osmolarity over time. In some embodiments, the polymorphs provided herein are stable for at least 1, 2, 3 or 4 weeks. For example, the polymorphs do not exhibit a change in one or more of polymorph form (e.g., an increase or decrease of a certain form), appearance, pH, percent impurities, activity (as measured by in vitro assays), or osmolarity over at least 1, 2, 3 or 4 weeks. In some embodiments, the polymorphs provided herein are stable for at least 1, 2, 3, 4, 5, 6, 7, 8, 9, 10, 11 or 12 months. For example, the polymorphs do not exhibit a change in one or more of polymorph form (e.g., an increase or decrease of a certain form), appearance, pH, percent impurities, activity (as measured by in vitro assays), or osmolarity over at least 1, 2, 3, 4, 5, 6, 7, 8, 9, 10, 11 or 12 months. In the above, the phrase "do not exhibit a change" refers to a change of less than 5% (e.g., less than 4%, less than 3%, less than 2%, less than 1%) as measured for any of the parameters over the relevant time period.

The crystallinity of a polymorph of the HCl salt of linaprazan glurate may be measured e.g. by X-ray powder diffraction (XRPD) methods or by differential scanning calorimetry (DSC) methods. When reference is made herein to a crystalline compound, preferably the crystallinity is greater than about 70%, such as greater than about 80%, particularly greater than about 90%, more particularly greater than about 95%. In some embodiments, the degree of crystallinity is greater than about 98%. In some embodiments, the degree of crystallinity is greater than about 99%. The % crystallinity refers to the percentage by weight of the total sample mass which is crystalline.

As used herein, the term "about" refers to a value or parameter herein that includes (and describes) embodiments that are directed to that value or parameter per se. For example, description referring to "about 20" includes description of "20." Numeric ranges are inclusive of the numbers defining the range. Generally speaking, the term "about" refers to the indicated value of the variable and to all values of the variable that are within the experimental error of the indicated value (e.g., within the 95% confidence interval for the mean) or within 10 percent of the indicated value, whichever is greater.

The invention will now be described by the following examples which do not limit the invention in any respect. All cited documents and references mentioned herein are incorporated by reference in their entireties.

Abbreviations

DMF N,N-dimethylformamide
DMSO dimethyl sulfoxide
EtOAc ethyl acetate
EtOH ethanol
MeOH methanol
RH relative humidity Experimental Methods General Methods $^1$H-NMR spectra were recorded on a Bruker 400 MHz instrument at 25° C. and referenced to residual protic solvent in the deuterated solvent used: DMSO-$d_6$ ($\delta_H$ 2.50 ppm).

Analytical HPLC-MS was performed using an Agilent 1100 series Liquid Chromatography/Mass Selective Detector (MSD) (Single Quadrupole) equipped with an electrospray interface and a UV diode array detector. Analyses were performed using an ACE 3 C8 (3.0×50 mm) column with a gradient of acetonitrile in 0.1% aqueous TFA over 3 minutes and a flow rate of 1 mL/minute.

For solubility studies, HPLC was performed using an Agilent 1100 series Liquid Chromatography system, equipped with DAD spectrometer. Analyses were performed using a Waters X Bridge BEH C18 column (4.6×100 mm, 2.5 μm) at 30° C. Mobile phase: A=0.1% formic acid in water, B=0.1% formic acid in acetonitrile. Flow rate 0.8 mL/min. Mobile phase program:

| Time (min) | % A | % B |
| --- | --- | --- |
| 0.0 | 95 | 5 |
| 1.5 | 95 | 5 |
| 10.0 | 5 | 95 |
| 12.0 | 5 | 95 |
| 12.5 | 95 | 5 |
| 15.0 | 95 | 5 |

X-Ray Powder Diffraction (XRPD) Analysis

Analyses were performed on a PanAlytical X'Pert Pro diffractometer equipped with a Cu-anode (45 kV, 40 mA), a Kα-1 Johansson monochromator (1.54060 Å) and a Pixcel detector. The 2-theta range was 2-35°, using a scan speed of 0.10°/s and a step size of 0.013°. Slow spinning sample holders were used. The samples were smeared out on zero background wafers of Si, producing a flat powdered surface. The measurements were performed using a programmable incident divergency slit.

It is known in the art that an X-ray powder diffraction pattern may be obtained having one or more measurement errors depending on measurement conditions (such as equipment, sample preparation or machine used). In particular, it is generally known that intensities in an XRPD pattern may fluctuate depending on measurement conditions and sample preparation. For example, persons skilled in the art of XRPD will realize that the relative intensities of peaks may vary according to the orientation of the sample under the test and on the type and setting of the instrument used. The skilled person will also realize that the position of reflections can be affected by the precise height at which the sample sits in the diffractometer and the zero calibration of the diffractometer. The surface planarity of the sample may also have a small effect. Hence a person skilled in the art will appreciate that the diffraction pattern presented herein is not to be construed as absolute and any crystalline form that provides a powder diffraction pattern substantially identical to those disclosed herein fall within the scope of the present disclosure (for further information, see R. Jenkins and R. L. Snyder, "Introduction to X-ray powder diffractometry", John Wiley & Sons, 1996).

Thermogravimetric Analysis (TGA)

Analyses were performed on a PerkinElmer TGA7 instrument. A few mg of sample was gently charged into open Pt-pans and analysed by weight in a flow of dry nitrogen gas (20 mL/min), to ensure an inert atmosphere. The sample was scanned from 25 to 200° C. using a continuous scan speed of 10° C./min.

Differential Scanning Calorimetry (DSC)

Analyses were performed on a Netzsch DSC 204F1 instrument. A few mg of sample was gently charged into, and weighed, in Al pans. A lid with pre-made pinhole was adapted and crimped onto the pan. Conventional DSC with a heating rate of 10° C./min was employed. Minimum temperature (start) was 0° C. and maximum temperature was 250° C.

Dynamic Vapour Sorption (DVS)

Analyses were performed on an SMS DVS-1 instrument. A few mg of the substance was added into an Al pan and exposed to stepwise RH changes during two identical consecutive cycles according to 0-10-20-30-40-50-60-70-80-90-80-70-60-50-40-30-20-10-0% RH using open loop mode. The experiments were performed using a gas flow rate of 200 mL/min and at 25° C. The dm/dt criteria applied was 0.001 weight-%/min during a 5-minutes window, with a maximum allowed time of 360 minutes and a minimum allowed time of 10 minutes for all steps.

EXAMPLES

Example 1

Preparation of the Hydrochloride Salt of Linaprazan Glurate

Linaprazan glurate (8.12 g, 16.9 mmol) was suspended in 2-propanol (200 mL) at 22° C., and the suspension was stirred. Aqueous HCl (12 M; 1.67 g, 16.9 mmol) was added, which produced a slurry. Stirring was continued for 2.5 hours. The suspension was then filtered through a P3 fritted glass filter funnel, and the solid was dried under vacuum. Yield: 94% (8.20 g; colourless powder); 100% purity according to LCMS.

$^1$H NMR (400 MHz, DMSO-$d_6$): δ 12.07 (s, 1H), 9.10 (t, J=5.6 Hz, 1H), 8.43 (d, J=1.2 Hz, 1H), 7.35 (s, 1H), 7.27-7.03 (m, 3H), 6.48 (s, 1H), 4.44 (d, J=3.9 Hz, 2H), 4.21 (t, J=5.7 Hz, 2H), 3.58 (q, J=5.7 Hz, 2H), 2.45-2.30 (m, 11H), 2.24 (t, J=7.4 Hz, 2H), 1.74 (p, J=7.4 Hz, 2H). MS: (ESI+) m/z 481 (M+H).

Example 2

Polymorph Screen

A polymorph screen was performed on the HCl salt of linaprazan glurate to determine solubility, polymorphism and thermodynamic stability.

X-ray powder diffraction (XRPD), thermogravimetric analysis (TGA) and differential scanning calorimetry (DSC) indicated that the drug substance used for the screen was a mixture of Form 1 and Form 2. A TGA scan showed a gradual weight loss of about 1% when heated to 140° C. (data not shown). Prior to the crystallisation experiments, the solubility of the drug substance was determined in >20 solvents and solvent mixtures.

Slurry Experiments:

Slurry experiments were performed in various solvents wherein the HCl salt of linaprazan glurate was found to have an intermediate solubility. Approximately 50 to 200 mg of the drug substance was slurried in 11 different solvents (pure and binary solvents) at room temperature and at 40° C. for 3 weeks, unless indicated otherwise. All solvents were dried by adding molecular sieves prior to preparing slurries, unless indicated otherwise. The solid phase was isolated and analysed with XRPD. Crystalline solid forms were obtained in the experiments shown in Table 1.

TABLE 1

Results of slurry experiments

| Solvent | Salt (mg) | Solvent volume (mL) | Temperature | Solid state form |
|---|---|---|---|---|
| MeOH | 99.6 | 1 | RT | Form 2 |
| MeOH | 96.0 | 0.5 | 40° C. | Form 2 |
| EtOH | 49.2 | 4 | RT | Form 2 |
| EtOH | 49.3 | 4 | 40° C. | Form 2 + small amount of Form 1 |
| EtOH | 52.4 | 3 | 40° C. | Form 2 * |
| Formamide | 96.7 | 1 | RT | Crystalline base form ** |
| Formamide | 99.6 | 0.5 | 40° C. | Crystalline base form ** |
| DMF | 101.2 | 0.5 | RT | Form 1 |
| DMF | 202.5 | 0.5 | 40° C. | Form 1 |
| Benzyl alcohol | 102.6 | 1 | RT | Form 1 |
| Benzyl alcohol | 106.2 | 0.5 | 40° C. | Form 1 |
| Pyridine | 197.2 | 0.5 | RT | Form 1 |
| DMSO | 102.4 | 1 | RT | DMSO solvate |
| DMSO | 101.5 | 0.5 | 40° C. | DMSO solvate |
| MeOH/water 9:1 | 51.3 | 2 | RT | Form 2 |
| MeOH/water 9:1 | 96.7 | 0.5 | 40° C. | Form 2 |
| DMF/water 8:2 | 107.7 | 1 | RT | Form 1 + Crystalline base form |
| DMF/water 8:2 | 102.0 | 0.5 | 40° C. | Crystalline base form *** |
| Pyridine/water 7:3 | 97.1 | | RT | Crystalline base form |
| Pyridine/water 7:3 | 102.8 | | 40° C. | Crystalline base form *** |
| Acetic acid | 102.5 | 1 | RT | Form 2 |
| Acetic acid | 102.1 | 0.5 | 40° C. | Form 2 * |

*: analysed after 2 weeks

**: same results obtained with dried and non-dried solvent

***: analysed after 1 week

Evaporation Experiments:

Experiments were performed in six solvents wherein the HCl salt of linaprazan glurate was found to have sufficiently high solubility. All solvents were dried by adding molecular sieves prior to preparing solutions, unless indicated otherwise. Approximately 10 or 20 mg of the drug substance was dissolved and left to evaporate for 10 days, either in the vial or directly on a XRPD zero background plate at room temperature and ambient relative humidity. The results are shown in Table 2.

TABLE 2

Results of evaporation experiments

| Solvent | Salt (mg) | Solvent volume (mL) | Solid state form |
|---|---|---|---|
| MeOH | 20.1 | 2 | Form 2 * |
| Formamide | 9.9 | 1 | Crystalline base form ** |
| DMF | 22.2 | 1 | Amorphous |
| Pyridine | 19.1 | 0.5 | Form 1 + Form 2 |
| Pyridine | 20.9 | 0.5 | Amorphous |
| DMSO | 9.3 | 1 | DMSO solvate |
| Benzyl alcohol | 9.9 | 1 | decomposed |

*: left to evaporate for 3 days
**: did not dissolve completely; same results obtained with dried and non-dried solvent Anti-Solvent Crystallisations:

Crystallisations were performed from certain solvents wherein the HCl salt of linaprazan glurate was found to have a high solubility, together with certain anti-solvents wherein the HCl salt of linaprazan glurate is practically insoluble. All solvents were dried by adding molecular sieves prior to performing the experiments.

The drug substance was dissolved in solvent 1 and solvent 2 was then added in 0.5 mL portions. As precipitation did not occur immediately in any of the experiments, the vials were placed at 5 CC to induce precipitation. If no crystals had formed after 4 days, a piece of metal wire was added to induce crystallisation and the vial was left for another 7 days. The solid phase was separated by vacuum filtration and analysed by XRPD. Crystalline solid forms were obtained in the experiments shown in Table 3.

TABLE 3

Results of antisolvent crystallisations

| Solvent 1 | Salt (mg) | Solvent 1 volume (mL) | Solvent 2 | Solvent 2 volume (mL) | Solid state form |
|---|---|---|---|---|---|
| MeOH | 20.7 | 2 | Water | 2 | Crystalline base form |
| MeOH | 21.0 | 2 | 2-propanol | 2 | Form 2 |
| MeOH | 21.2 | 2 | Acetone | 2 | Form 2 |
| MeOH | 20.1 | 2 | EtOAc | 2 | Form 2 |
| DMF | 51.9 | 2 | Water | 2 | Crystalline base form |
| DMF | 51.8 | 2 | 2-propanol | 2 | Form 1 |
| DMF | 51.7 | 2 | Acetone | 2 | Form 1 |
| DMF | 50.2 | 2 | EtOAc | 2 | Form 1 |
| Pyridine | 51.1 | 1 | Water | 2 | Crystalline base form |
| Pyridine | 51.1 | 1 | 2-propanol | 2 | Form 1 |
| Pyridine | 51.1 | 1 | Acetone | 2 | Form 1 |
| Pyridine | 51.7 | 1 | EtOAc | 2 | Form 1 |
| Pyridine | 50.1 | 1 | Heptane | 2 | Form 1 |
| Pyridine | 101.8 | 1 | Water | 1 | Crystalline base form |
| DMSO | 20.1 | 2 | Water | 2 | Crystalline base form |
| DMSO | 21.3 | 2 | 2-propanol | 2 | DMSO solvate |
| DMSO | 20.1 | 2 | Acetone | 2 | DMSO solvate |
| DMSO | 21.0 | 2 | EtOAc | 2 | DMSO solvate |

Cooling Experiments:

Cooling experiments were performed in solvents and solvent mixtures wherein the solubility of the HCl salt of linaprazan glurate was found high enough to dissolve a reasonable amount. All solvents were dried by adding molecular sieves prior to preparing solutions, unless indicated otherwise. Samples were prepared where most of the drug substance was dissolved at room temperature. The temperature was then increased to 40° C. to dissolve the drug substance completely. The vials were placed in a refrigerator at 5° C., except for the DMSO solution that was placed at room temperature. The solid phase was separated by vacuum filtration and analysed by XRPD. Crystalline solid forms were obtained in the experiments shown in Table 4.

TABLE 4

Results of cooling experiments

| Solvent | Salt (mg) | Solvent volume (mL) | Solid state form |
|---|---|---|---|
| MeOH/water 9:1 | 48.9 | 1 | Form 2 * |
| MeOH | 51.9 | 1.5 | Form 2 |
| Formamide (non-dried) | 49.8 | 3 | Crystalline base form ** |
| Formamide | 48.6 | 1 | Crystalline base form ** |
| DMF | 99.2 | 1 | Form 1 * |
| Pyridine | 102.1 | 0.5 | Form 1 * |
| DMSO | 52.4 | 1 | DMSO solvate |

*: a piece of metal wire was added to induce crystallisation after several days at 5° C.
**: did not dissolve at 40° C. The solid obtained at 40° C. was analysed.

The XRPD peaks for Form 1, as obtained from a slurry in DMF at 40° C., are listed in Table 5 below. The diffractogram for Form 1 is shown in FIG. 1.

TABLE 5

XRPD peaks for Form 1

| Position [°2θ] | Height [cts] | FWHM Left [°2θ] | d-spacing [Å] | Rel. Int. * [%] |
|---|---|---|---|---|
| 3.77 | 562.3 | 0.090 | 23.42 | 10.7 |
| 9.09 | 993.6 | 0.078 | 9.72 | 19.0 |
| 10.30 | 350.2 | 0.078 | 8.58 | 6.7 |

TABLE 5-continued

XRPD peaks for Form 1

| Position [°2θ] | Height [cts] | FWHM Left [°2θ] | d-spacing [Å] | Rel. Int. * [%] |
|---|---|---|---|---|
| 11.67 | 190.4 | 0.125 | 7.58 | 3.6 |
| 12.60 | 179.0 | 0.156 | 7.02 | 3.4 |
| 13.84 | 1014.3 | 0.047 | 6.39 | 19.4 |
| 13.99 | 813.9 | 0.062 | 6.37 | 15.5 |
| 15.72 | 329.6 | 0.094 | 5.63 | 6.3 |
| 16.19 | 395.1 | 0.090 | 5.47 | 7.5 |
| 18.55 | 403.1 | 0.078 | 4.78 | 7.7 |
| 20.01 | 5241.6 | 0.062 | 4.43 | 100 |
| 20.55 | 331.8 | 0.094 | 4.32 | 6.3 |
| 22.21 | 399.3 | 0.078 | 4.00 | 7.6 |
| 22.45 | 259.3 | 0.078 | 3.96 | 5.0 |
| 22.89 | 663.6 | 0.078 | 3.88 | 12.7 |
| 23.11 | 216.4 | 0.090 | 3.85 | 4.1 |
| 23.45 | 900.2 | 0.109 | 3.79 | 17.2 |
| 24.38 | 1327.5 | 0.094 | 3.65 | 25.3 |
| 24.55 | 1176.2 | 0.094 | 3.622 | 22.4 |
| 24.92 | 355.6 | 0.078 | 3.57 | 6.8 |
| 25.56 | 373.5 | 0.094 | 3.48 | 7.1 |
| 26.68 | 1858.1 | 0.062 | 3.34 | 35.5 |
| 27.64 | 203.4 | 0.125 | 3.22 | 3.9 |
| 27.90 | 378.6 | 0.078 | 3.20 | 7.2 |

* The relative intensity depends on the particle orientation, crystallite size/shape, strain and specimen thickness The XRPD peaks for Form 2, as obtained by cooling from MeOH/water 9:1 ("sample 1") are listed in Table 6 below. The diffractogram for Form 2, sample 1 is shown in FIG. 2.

TABLE 6

XRPD peaks for Form 2, sample 1

| Position [°2θ] | Height [cts] | FWHM Left [°2θ] | d-spacing [Å] | Rel. Int. * [%] |
|---|---|---|---|---|
| 7.14 | 3055.7 | 0.094 | 12.37 | 100 |
| 9.93 | 892.3 | 0.172 | 8.90 | 29.2 |
| 10.26 | 771.2 | 0.109 | 8.61 | 25.2 |
| 11.39 | 224.0 | 0.094 | 7.76 | 7.3 |
| 12.08 | 239.1 | 0.078 | 7.32 | 7.8 |
| 13.90 | 142.1 | 0.125 | 6.37 | 4.7 |
| 14.25 | 365.9 | 0.078 | 6.21 | 12.0 |
| 14.83 | 538.3 | 0.078 | 5.97 | 17.6 |
| 15.00 | 1133.4 | 0.078 | 5.90 | 37.1 |
| 15.74 | 488.7 | 0.109 | 5.63 | 16.0 |
| 16.17 | 188.4 | 0.125 | 5.48 | 6.2 |
| 18.90 | 227.6 | 0.078 | 4.69 | 7.5 |
| 20.53 | 199.0 | 0.125 | 4.32 | 6.5 |
| 20.77 | 258.0 | 0.094 | 4.27 | 8.4 |
| 21.15 | 164.4 | 0.187 | 4.20 | 5.4 |
| 22.64 | 591.8 | 0.078 | 3.92 | 19.4 |
| 22.84 | 658.1 | 0.094 | 3.89 | 21.5 |
| 23.58 | 180.0 | 0.125 | 3.77 | 5.9 |
| 24.94 | 1264.4 | 0.094 | 3.57 | 41.4 |
| 25.43 | 658.6 | 0.094 | 3.50 | 21.6 |
| 26.87 | 371.2 | 0.078 | 3.32 | 12.2 |
| 27.28 | 340.9 | 0.078 | 3.27 | 11.2 |
| 27.64 | 320.9 | 0.109 | 3.22 | 10.5 |
| 28.92 | 417.7 | 0.078 | 3.09 | 13.7 |
| 29.37 | 287.0 | 0.078 | 3.04 | 9.4 |
| 29.83 | 380.5 | 0.078 | 2.99 | 12.5 |

* The relative intensity depends on the particle orientation, crystallite size/shape, strain and specimen thickness The XRPD peaks for Form 2, as obtained by cooling from MeOH ("sample 2") are listed in Table 7 below. The diffractogram for Form 2, sample 2 is shown in FIG. 3.

TABLE 7

XRPD peaks for Form 2, sample 2

| Position [°2θ] | Height [cts] | FWHM Left [°2θ] | d-spacing [Å] | Rel. Int. * [%] |
|---|---|---|---|---|
| 7.11 | 4615.3 | 0.094 | 12.43 | 100 |
| 9.91 | 1821.1 | 0.094 | 8.92 | 39.5 |
| 10.15 | 1147.9 | 0.094 | 8.71 | 24.9 |
| 11.03 | 351.4 | 0.156 | 8.02 | 7.6 |
| 11.30 | 361.9 | 0.094 | 7.83 | 7.8 |
| 12.14 | 353.5 | 0.078 | 7.29 | 7.7 |
| 13.97 | 255.3 | 0.078 | 6.34 | 5.5 |
| 14.16 | 703.9 | 0.109 | 6.25 | 15.3 |
| 14.85 | 1012.5 | 0.062 | 5.96 | 21.9 |
| 14.99 | 2128.0 | 0.094 | 5.91 | 46.1 |
| 15.71 | 1076.5 | 0.094 | 5.64 | 23.3 |
| 16.00 | 674.9 | 0.078 | 5.53 | 14.6 |
| 17.28 | 194.0 | 0.078 | 5.13 | 4.2 |
| 18.17 | 301.4 | 0.109 | 4.88 | 6.5 |
| 18.82 | 526.7 | 0.094 | 4.71 | 11.4 |
| 20.50 | 367.1 | 0.094 | 4.33 | 8.0 |
| 20.70 | 672.2 | 0.094 | 4.29 | 14.6 |
| 20.92 | 310.6 | 0.094 | 4.24 | 6.7 |
| 22.10 | 448.4 | 0.078 | 4.02 | 9.7 |
| 22.63 | 2708.6 | 0.094 | 3.93 | 58.7 |
| 22.77 | 1141.0 | 0.078 | 3.90 | 24.7 |
| 23.51 | 473.3 | 0.094 | 3.78 | 10.3 |
| 24.37 | 357.9 | 0.156 | 3.65 | 7.8 |
| 24.98 | 2321.8 | 0.094 | 3.56 | 50.3 |
| 25.25 | 752.6 | 0.094 | 3.52 | 16.3 |
| 25.38 | 408.1 | 0.090 | 3.51 | 8.8 |
| 25.49 | 465.2 | 0.062 | 3.49 | 10.1 |
| 26.91 | 811.0 | 0.094 | 3.31 | 17.6 |
| 27.15 | 568.5 | 0.078 | 3.28 | 12.3 |
| 27.38 | 1059.4 | 0.078 | 3.26 | 23.0 |
| 27.81 | 196.4 | 0.094 | 3.21 | 4.3 |
| 28.43 | 493.0 | 0.062 | 3.14 | 10.7 |
| 28.89 | 740.9 | 0.078 | 3.09 | 16.1 |
| 29.26 | 718.1 | 0.094 | 3.05 | 15.6 |
| 29.59 | 1103.5 | 0.094 | 3.02 | 23.9 |
| 29.93 | 339.6 | 0.078 | 2.98 | 7.4 |
| 32.27 | 344.0 | 0.125 | 2.77 | 7.5 |
| 32.46 | 323.8 | 0.078 | 2.76 | 7.0 |
| 33.83 | 351.0 | 0.062 | 2.65 | 7.6 |

* The relative intensity depends on the particle orientation, crystallite size/shape, strain and specimen thickness The DMSO solvate that was obtained in certain experiments was a highly crystalline solid form but was not considered pharmaceutically viable. TGA experiments confirmed that this form contains about 1 mole of DMSO per mole of HCl salt of linaprazan glurate. After the heating of the sample in the TGA experiment, it was found that the X-ray powder diffractogram of the dried sample was identical to that of Form 1 (data not shown).

Example 3

Thermogravimetric Analysis

Figure 4:
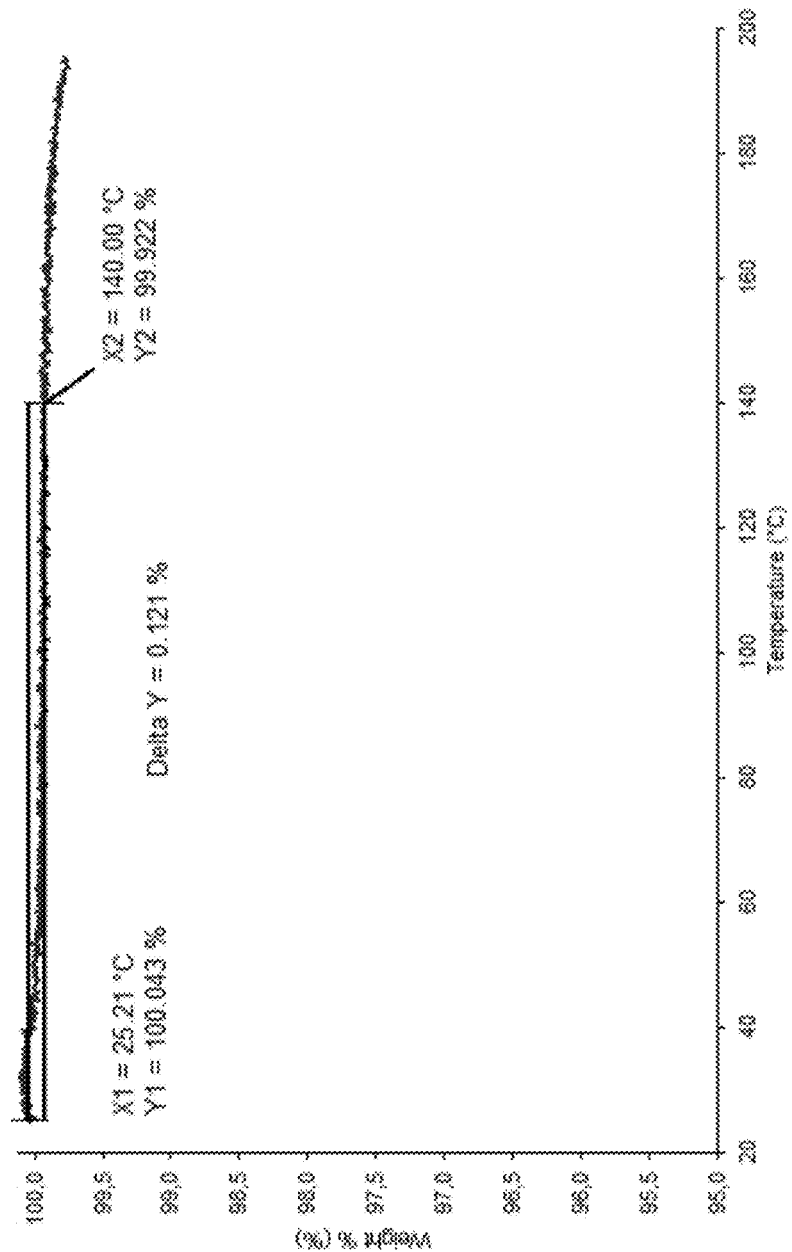
FIG. 4 shows the thermogravimetric analysis (TGA) weight loss curve of Form 1, as crystallized from DMF using EtOAc as the anti-solvent.

A sample of Form 1 (obtained by crystallisation from DMF using EtOAc as the anti-solvent) showed a weight loss of 0.1% upon heating from 30 to 140° C. This confirms that Form 1 is an anhydrate. The TGA weight loss curve for Form 1 is shown in FIG. 4.

Figure 5:
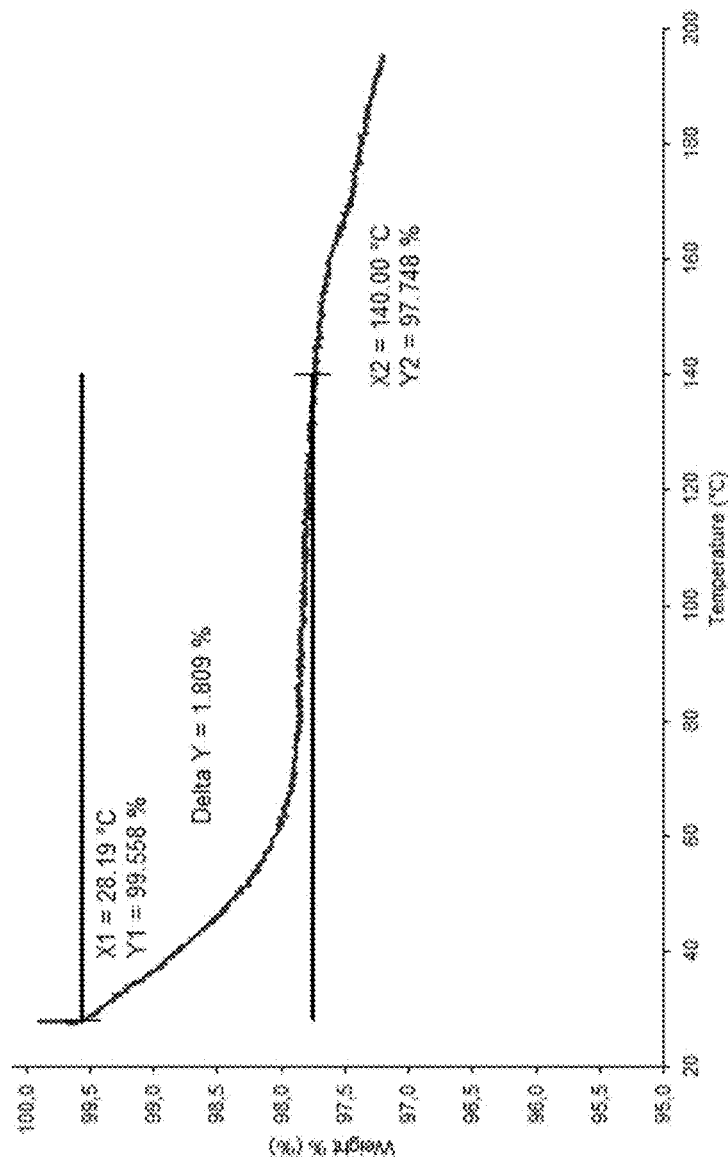
FIG. 5 shows the TGA weight loss curve of Form 2, sample 1.
Figure 6:
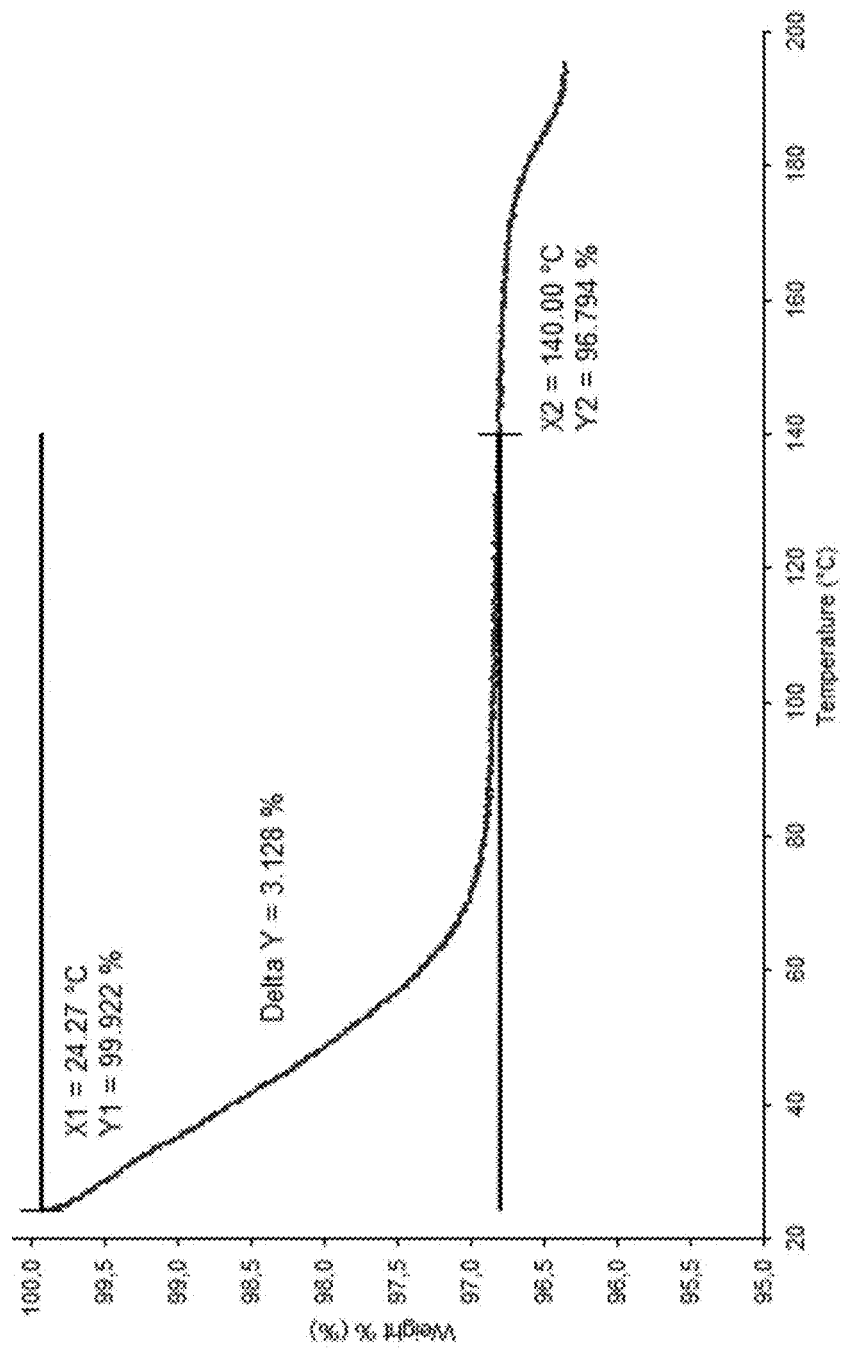
FIG. 6 shows the TGA weight loss curve of Form 2, sample 2.

Samples 1 and 2 of Form 2 showed weight losses of 1.8 and 3.1%, respectively, upon heating from 30 to 140° C. This weight loss is attributed to the release of water. The difference between the two samples probably depends on different relative humidities at the time of analysis of the samples. Weight losses at higher temperature are likely due to decomposition of the sample. The TGA weight loss curves for samples 1 and 2 of Form 2 are shown in FIGS. 5 and 6, respectively.

After the TGA experiment, sample 2 of Form 2 was analysed by XRPD. It was found that the diffractogram for the dried sample was identical to the diffractogram obtained for Form 1 (data not shown).

Example 4

Differential Scanning Calorimetry (DSC) Analysis

Figure 7:
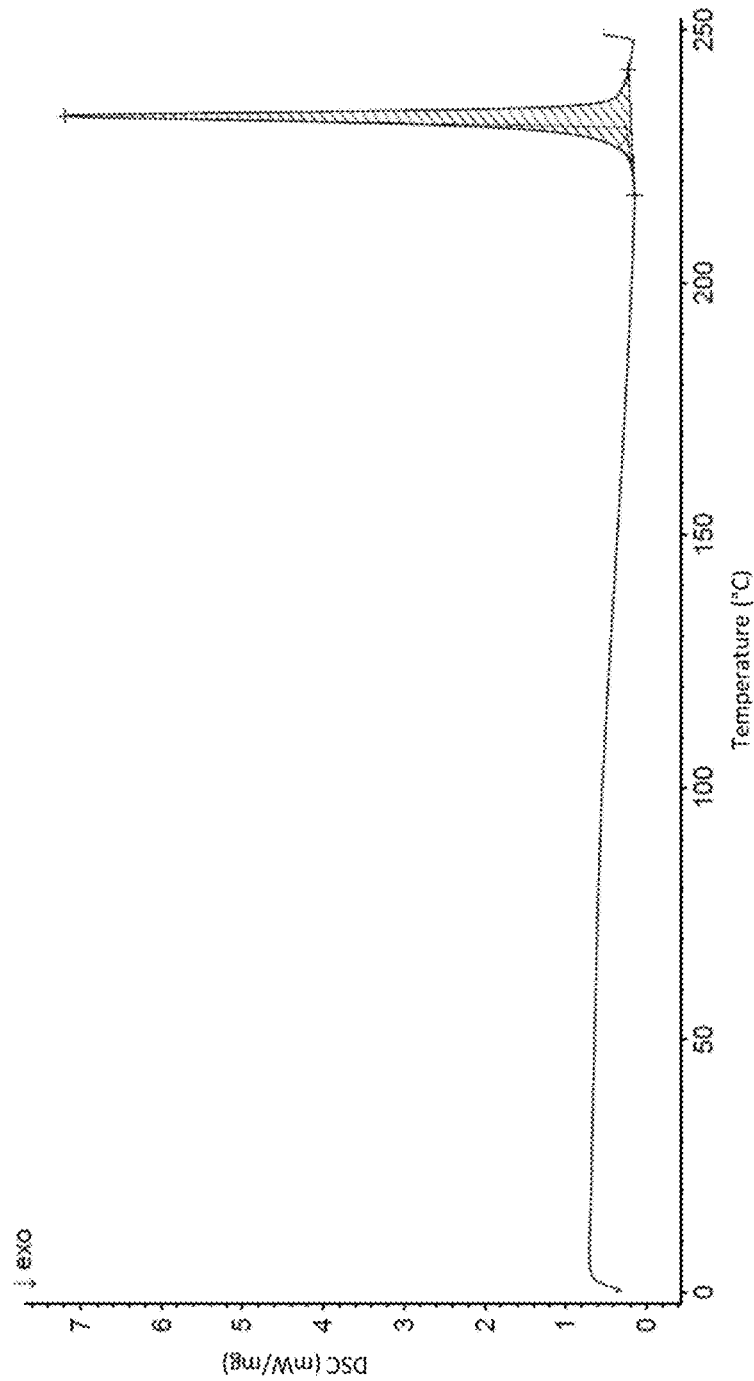
FIG. 7 shows the differential scanning calorimetry (DSC) thermogram of Form 1, as crystallized from DMF using EtOAc as the anti-solvent.

A sample of Form 1 (obtained by crystallisation from DMF using EtOAc as the anti-solvent) displayed a single endothermic event at approximately 233° C. (onset 230.7° C.), which may be attributed to the melting of an anhydrous HCl salt. The DSC thermogram is shown in FIG. 7.

Figure 8:
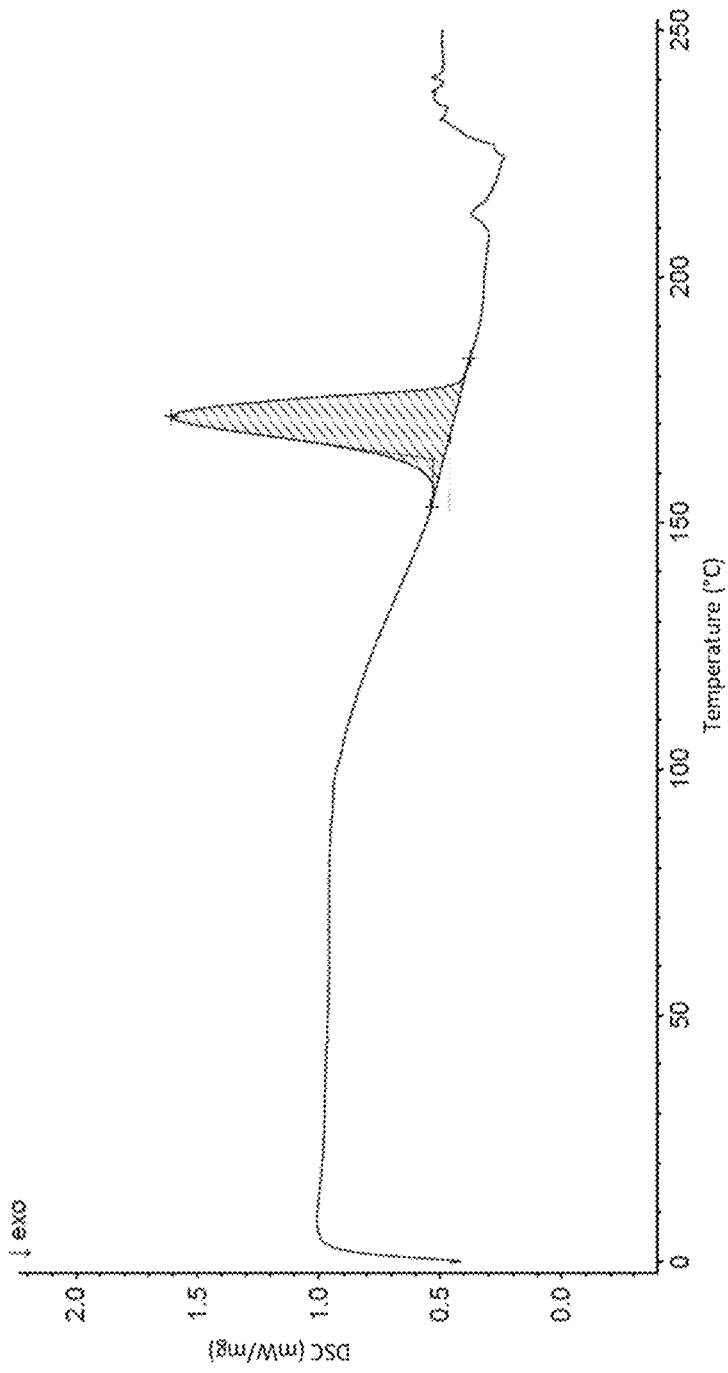
FIG. 8 shows the differential scanning calorimetry (DSC) thermogram of Form 2, sample 1.
Figure 9:
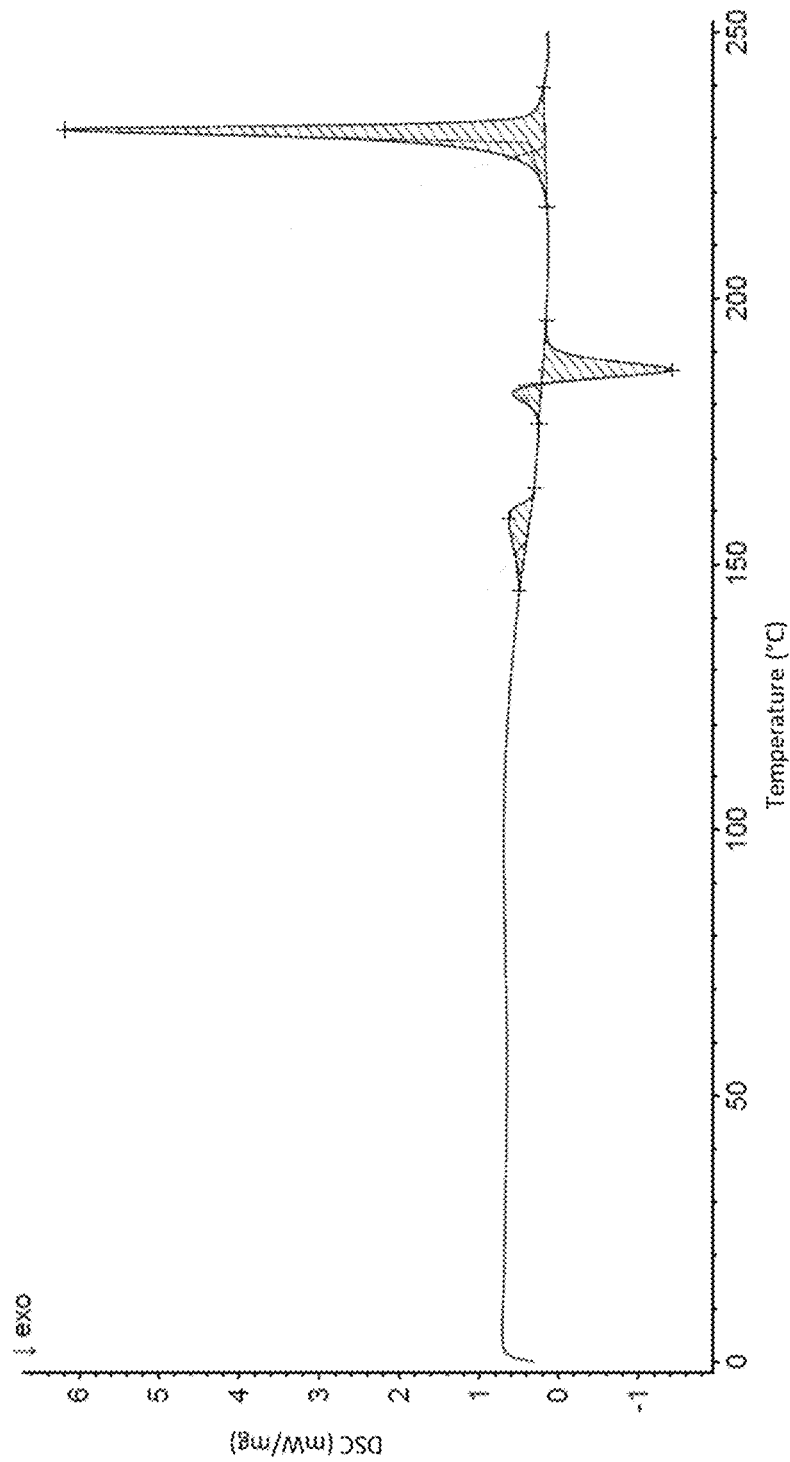
FIG. 9 shows the differential scanning calorimetry (DSC) thermogram of Form 2, sample 2.

For Form 2, samples 1 and 2 were investigated. The DSC thermograms are shown in FIGS. 8 and 9, respectively. Sample 1 showed only one endothermic event attributed to melting of form 2. The event is broad, suggesting that some water remains when the melting starts and then is released during the melting process. The event has a peak at approximately 171-172° C. (onset 163.0° C.). Sample 2 showed a more complex thermal behaviour. The first small endotherm at about 150° C. may be attributed to release of water. The second event that starts at approximately 180° C. is interpreted as a melting of Form 2 (endothermic) overlapping with a recrystallisation to Form 1 (exothermic). The final endothermic event is melting of Form 1. The melting temperature of approximately 232° C. (onset 229.3° C.) is in accordance with what was found for Form 1 (see FIG. 7).

Example 5

Dynamic Vapour Sorption (DVS) Analysis

Figure 10A:
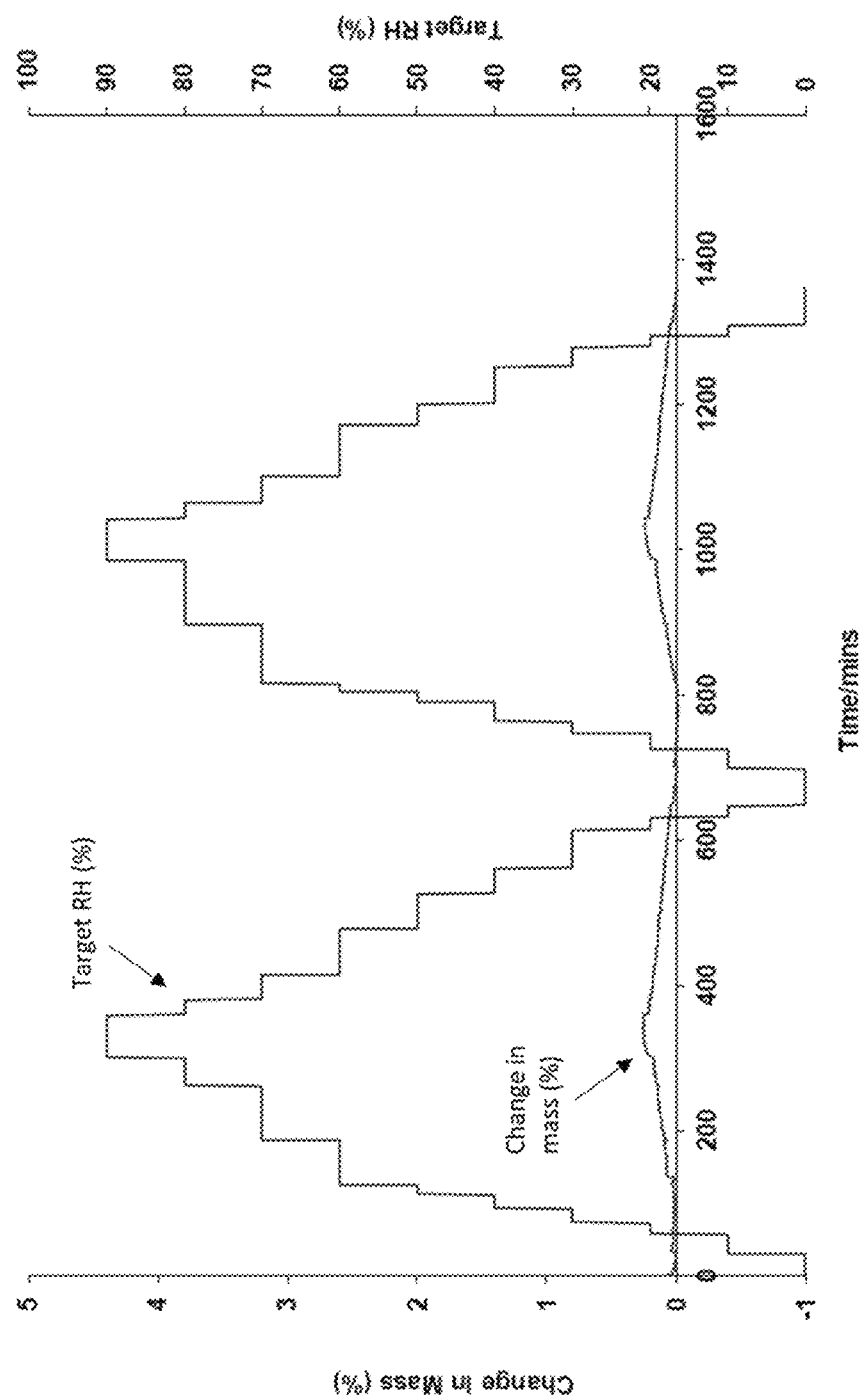
FIG. 10A shows the dynamic vapour sorption (DVS) weight change plot, and FIG. 10B the DVS isotherm plot for Form 1, as crystallized from DMF using EtOAc as the anti-solvent.
Figure 10B:
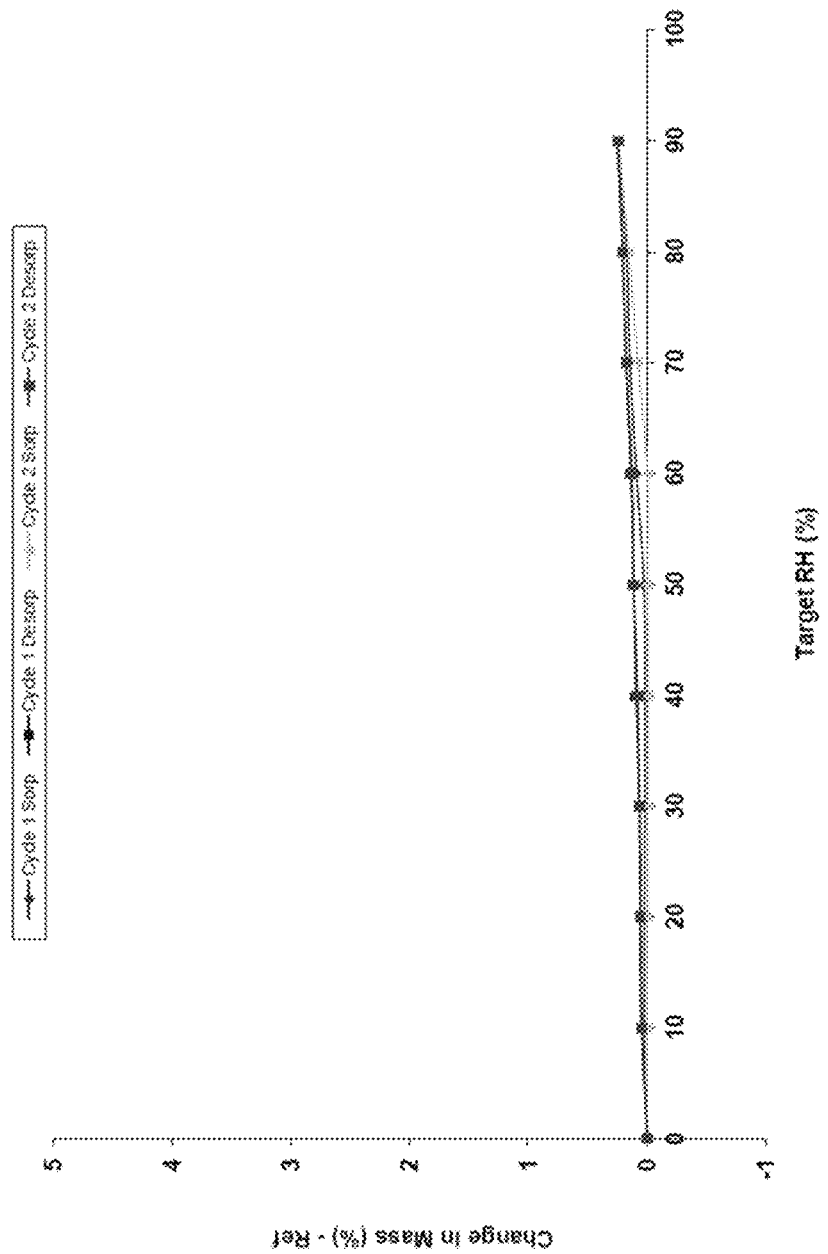

The hygroscopicity of Form 1 (obtained by crystallisation from DMF using EtOAc as the anti-solvent) and Form 2 (obtained from a slurry in MeOH) was investigated using DVS at 25° C. The weight change plot and the sorption isotherm plot for Form 1 showed only a small uptake of water at elevated humidities; see FIGS. 10A and 10B, respectively. With a water uptake of 0.2% at 90% RH, Form 1 can be classified as non-hygroscopic.

Figure 11A:
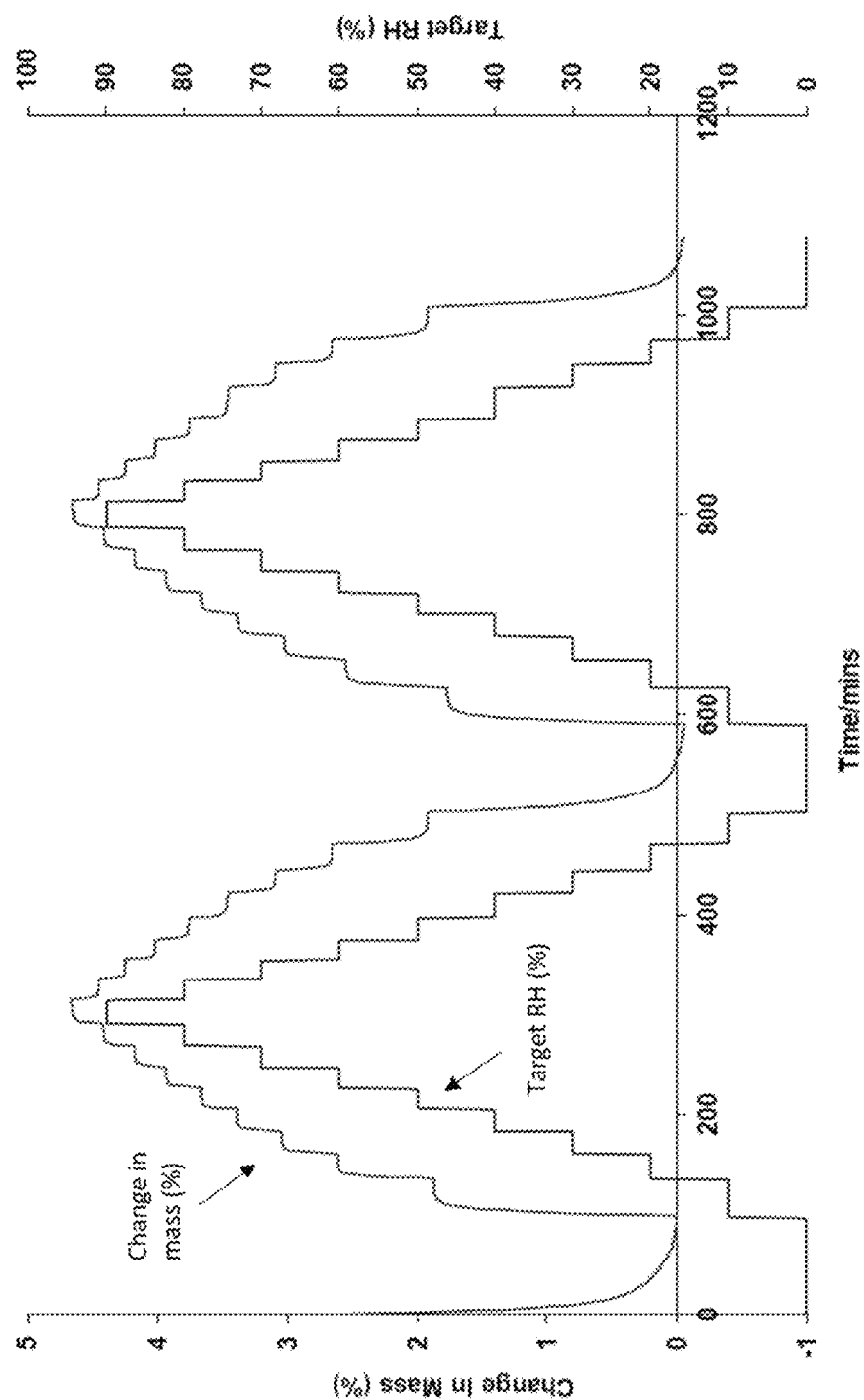
FIG. 11A shows the DVS weight change plot, and FIG. 11B the DVS isotherm plot for Form 2, as obtained from a slurry in MeOH.
Figure 11B:
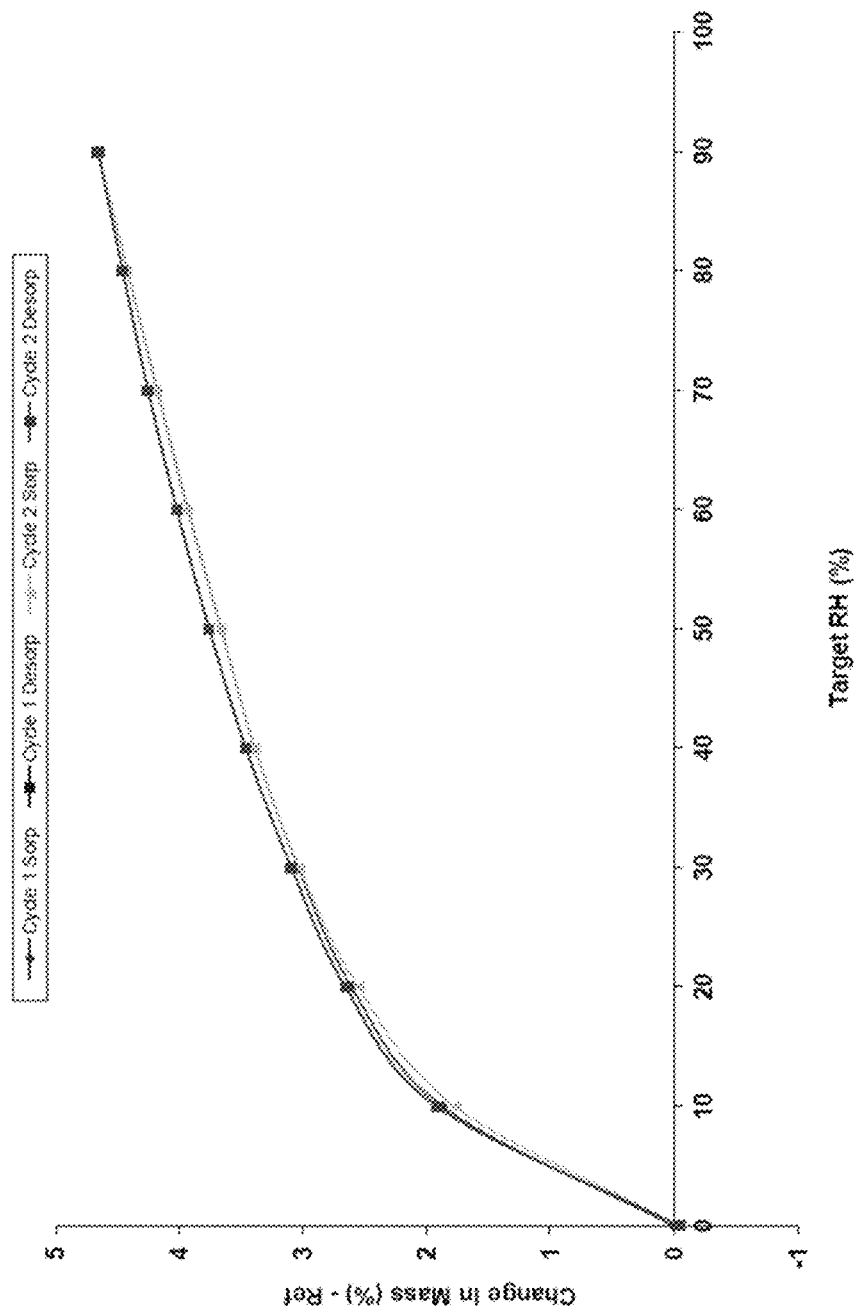

For Form 2, the weight change plot and the sorption isotherm plot (FIGS. 11A and 11B, respectively) showed a significant uptake of water at elevated humidities. The water uptake is rapid when the relative humidity is increased, and the water loss is equally rapid when the relative humidity is decreased. The sorption behaviour is typical for a channel hydrate, where the crystal structure adapts to accommodate different amounts of water depending on the surrounding humidity. The water uptake of 4.7% at 90% RH corresponds to 1.3 water molecules per linaprazan glurate HCl unit.

Example 6

Large Scale Preparation of Form 1

Step 1:

To a 250 L reactor, acetic acid (142.75 kg) and linaprazan glurate (crude product; 28.50 kg) were charged. More acetic acid was added (28.55 kg), and the mixture was heated to 30° C. and stirred at that temperature until a clear solution was obtained. The solution was filtered and the filtrate was transferred to a 500 L reactor. The first reactor was rinsed with additional acetic acid (14.17 kg). Ethyl acetate (199.40 kg) was then charged to the reactor. A solution of HCl in acetic acid (10.9% w/w, 19.44 kg) was then added dropwise to the reactor over 2 hours. The mixture was thereafter stirred at 30° C. for 2 hours. The mixture was filtered by centrifugation and the wet cake was washed with ethyl acetate (28.44 kg).

Step 2:

The reactor was charged with ethyl acetate (285 kg) and the wet cake of step 1 (37.98 kg), and seed crystals of Form 1 (0. kg/kg) were added. More ethyl acetate (28.49 kg) was added. The suspension was then slurried at 30° C. for 16 h. Additional ethyl acetate (85.5 kg) was added as the material got sticky. The suspension was filtered by centrifugation and the wet cake was washed with ethyl acetate (28.56 kg). The wet cake was dried at 65° C. under vacuum. A white solid was obtained (28.5 kg, 93.1% yield, Form 1).

Example 7

Solubility Studies

I. Solubility of Free Base and HCl Salt of Linaprazan Glurate in Media Simulating Gastric Fluid The solubility of the crystalline free base (Form A) and the crystalline HCl salt of linaprazan glurate (mixture of Forms 1 and 2) was studied in Fasted State Simulated Gastric Fluid (FaSSGF, Biorelevant, batch FFF-0119-B; pH 1.6) and Fed State Gastric Acid (FeDSGA, Biorelevant, batch FEDGAS-120-A; pH 5.0).

Sample Preparation, Analysis and Results

Saturated solutions were prepared in 4 mL vials by adding a fixed weight of the crystalline base or the crystalline HCl salt to 2 mL of each of the different buffer solutions. Vials were sonicated for 10 minutes and then stirred with a magnetic stirrer on a water bath (37° C.) for 24 hours. Samples were taken after 1, 4 and 24 hours, in replicates, and analysed by HPLC-UV. Concentrations were calculated from a calibration curve, constructed using 8 calibration standards (serial dilutions of stock solutions of the free base and the HCl salt of linaprazan glurate).

It was found that the free base had a higher solubility in FaSSGF, but that the HCl salt had a higher solubility in FeDSGA. The difference was most significant after 1 hour: in FaSSGF, the solubility of the free base was about 1.4 times higher than the solubility of the HCl salt, whereas in FeDSGA the solubility of the HCl salt was more than 6.5 times higher than the solubility of the free base. The results are shown in FIG. 12.

II. Solubility of Form 1 and Form 2 in Media Simulating Gastric and Intestinal Fluids.

The solubility of the two crystalline HCl salts of linaprazan glurate in Fed State Simulated Gastric Fluid (FEDGAS) mid stage, second version of Fasted State Simulated Intestinal Fluid (FaSSIF-V2) and second version of Fed State Simulated Intestinal Fluid (FeSSIF-V2) was studied.

Preparation of Buffer Solutions

FaSSIF-V2:

To 90 mL of Milli Q water were added 139 mg of NaOH, 222 mg of maleic acid and 401 mg of NaCl and the resulting mixture was stirred until fully dissolved. The pH was adjusted to 6.5 with 1 M HCl and 1 M NaOH, and made up to 100 mL with Milli Q water. 179 mg of FaSSIF-V2 (Biorelevant, batch V2FAS-1020-A) was mixed with the prepared 100 mL of buffer, stirred until fully dissolved and equilibrated at RT for 1 hour before use.

FeSSIF-V2:

To 90 mL of Milli Q water were added 327 mg of NaOH, 639 mg of maleic acid and 733 mg of NaCl and the resulting mixture was stirred until fully dissolved. The pH was adjusted to 5.8 with 1 M HCl and 1 M NaOH, and made up to 100 mL with Milli Q water. 976 mg of FeSSIF-V2

(Biorelevant, batch V2FES-1020-A) was mixed with the prepared 100 mL of buffer, stirred until fully dissolved and equilibrated at RT for 1 hour before use.

FEDGAS (Mid Stage, pH 4.5):

3.68 g of FEDGAS buffer concentrate (Biorelevant, batch FEDBUF45-0122-A), 73.1 g of Milli Q water and 15.3 g of FEDGAS gel (Biorelevant, batch FEDGAS-0322-A) were mixed thoroughly. The medium was stored at 37° C. before use.

Sample Preparation, Analysis and Results

Saturated solutions were prepared in 4 mL vials by adding fixed weights (excess amounts) of Form 1 or Form 2 to 2 mL of each of the different buffer solutions. Each experiment was performed in duplicate. The solutions were stirred with a magnetic stirring bar at 37° C. for 24 hours. Samples were taken after 1, 3, 6 and 24 hours. At each sampling point, 200 µL of sample solution was filtered using 0.2 µm PP syringeless filters. The filtered sample solutions were diluted 2 or 5 times with DMA and then analysed by HPLC-UV to determine the concentration of linaprazan glurate. Concentrations were calculated from a calibration curve based on 7 calibration standards (stock solutions of 100 and 250 µg/mL, and serial dilutions thereof).

It was found that the solubility of each of Forms 1 and 2 in FEDGAS was about 20-25 times higher than in FaSSIF-V2 and about 7-8 times higher than in FeSSIF-V2. The results are shown in FIG. 13A (Form 1) and FIG. 13B (Form 2).

The invention claimed is:

1. A crystalline HCl salt of linaprazan glurate which is Form 1, having an XRPD pattern, obtained with CuKα1-radiation, with at least two peaks at °2θ values selected from the list consisting of 3.8±0.2, 9.1±0.2, 13.8±0.2, 14.0±0.2, 20.0±0.2, 22.9±0.2, 23.4±0.2, 24.4±0.2, 24.6±0.2 and 26.7±0.2.

2. The crystalline HCl salt of linaprazan glurate according to claim 1, wherein Form 1 has an XRPD pattern, obtained with CuKα-radiation, with at least peaks at °2θ values of 20.0±0.2, 24.4±0.2, 24.6±0.2 and 26.7±0.2.

3. The crystalline HCl salt of linaprazan glurate according to claim 1, wherein Form 1 has an XRPD pattern, obtained with CuKα-radiation, with at least peaks at °2θ values of 9.1±0.2, 13.8±0.2, 20.0±0.2, 23.4±0.2, 24.4±0.2, 24.6±0.2 and 26.7±0.2.

4. A crystalline HCl salt of linaprazan glurate which is Form 1, having an XRPD pattern, obtained with CuKα-radiation, substantially as shown in FIG. 1.

5. The crystalline HCl salt of linaprazan glurate according to claim 1 wherein Form 1 has a DSC curve comprising an endotherm between about 230° C. and about 240° C., such as at approximately 233° C.

6. A crystalline HCl salt of linaprazan glurate which is Form 2, having an XRPD pattern, obtained with CuKα1-radiation, with at least two peaks at °2θ values selected from the list consisting of 7.1±0.2, 9.9±0.2, 10.2±0.2, 15.0±0.2, 15.7±0.2, 22.6±0.2, 22.8±0.2 and 25.0±0.2.

7. The crystalline HCl salt of linaprazan glurate according to claim 6, wherein Form 2 has an XRPD pattern, obtained with CuKα1-radiation, with at least peaks at °2θ values of 7.1±0.2, 15.0±0.2, 22.6±0.2 and 25.0±0.2.

8. The crystalline HCl salt of linaprazan glurate according to claim 6, wherein Form 2 has an XRPD pattern, obtained with CuKα1-radiation, with at least peaks at °2θ values of 7.1±0.2, 9.9±0.2, 10.2±0.2, 15.0±0.2, 15.7±0.2, 22.6±0.2, 22.8±0.2 and 25.0±0.2.

9. The crystalline HCl salt of linaprazan glurate according to claim 6, which is Form 2, having an XRPD pattern, obtained with CuKα-radiation, substantially as shown in FIG. 2 or FIG. 3.

10. The crystalline HCl salt of linaprazan glurate according to claim 6, wherein Form 2 has a DSC curve comprising an endotherm between about 175° C. and about 185° C., such as at approximately 180° C.

11. The crystalline HCl salt of linaprazan glurate according to claim 1, having a crystallinity of greater than 99%.

12. A pharmaceutical composition comprising a therapeutically effective amount of a crystalline HCl salt of linaprazan glurate according to claim 1, in association with one or more pharmaceutically acceptable excipients.

13. The crystalline HCl salt of linaprazan glurate according to claim 6, having a crystallinity of greater than 99%.

14. A pharmaceutical composition comprising a therapeutically effective amount of a crystalline HCl salt of linaprazan glurate according to claim 6, in association with one or more pharmaceutically acceptable excipients.

* * * * *